(12) United States Patent
Suhadolnik et al.

(10) Patent No.: US 6,362,171 B1
(45) Date of Patent: Mar. 26, 2002

(54) AMINOAKLANOYL-LINKED CONJUGATES OF 2′,5′-OLIGOADENYLATE AND ANTIVIRAL USES THEREOF

(75) Inventors: Robert J. Suhadolnik, Roslyn, PA (US); Wolfgang Pfleiderer, Constance (DE)

(73) Assignee: Temple University-of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/445,559

(22) PCT Filed: Jun. 1, 1998

(86) PCT No.: PCT/US98/11079

§ 371 Date: Dec. 9, 1999

§ 102(e) Date: Dec. 9, 1999

(87) PCT Pub. No.: WO98/56384

PCT Pub. Date: Dec. 17, 1998

Related U.S. Application Data

(60) Provisional application No. 60/049,745, filed on Jun. 12, 1997, and provisional application No. 60/052,043, filed on Jul. 9, 1997.

(51) Int. Cl.[7] ............ A61K 31/505; A61K 31/675; C07D 403/14; C07H 21/04
(52) U.S. Cl. .......... 514/44; 514/102; 536/25.6; 544/244
(58) Field of Search ............. 544/244; 536/25.6; 514/44, 102

(56) References Cited

U.S. PATENT DOCUMENTS

| | | | |
|---|---|---|---|
| 4,464,359 A | 8/1984 | Suhadolnik et al. | 424/180 |
| 4,859,768 A | 8/1989 | Suhadolnik et al. | 536/27 |
| 4,924,624 A | 5/1990 | Suhadolnik et al. | 47/58 |
| 4,981,957 A | 1/1991 | Lebleu et al. | 536/27 |

FOREIGN PATENT DOCUMENTS

| | | |
|---|---|---|
| GB | 2 002 773 A | 2/1979 |
| WO | WO 89/12380 | 12/1989 |
| WO | WO 93/17692 | 9/1993 |
| WO | WO 96/08256 | 3/1996 |

OTHER PUBLICATIONS

Wasner et al.:"6–Aminohexanoyl–Linked Conjugates of Monomeric and Trimeric Cordycepin"; Helve.Chim.Acta, 80/4, 1061–72(Jun. 30, 1997).*
Horndler et al., "59. Nucleotides", *Helvetica Chimica Acta*, 80:767–785 (May 12, 1997).
Wasner et al., "55. Nucleotides", *Heletica Chimica Acta*, 79:619–633 (May 8, 1996).
Wasner et al., "79. Nucleotides", *Helvetica Chimica Acta*, 80:1061–1072 (Jun. 30, 1997).
Wasner et al., "156. Nucleotides", *Heletica Chimica Acta*, 77:1757–1767 (1994).
Wasner et al., "54. Nucleosides" *Heletica Chimica Acta*, 79:609–618 (May 8, 1996).
Wasner and Pfleiderer, "Synthesis of Trimeric Cordycepin–Vitamin Conjugates as Improved Antiviral Agents", *Nucleosides & Nucleotides*, 14 (3–5):1101–1104 (1995).
Beaucage and Iyer, "The Functionalization of Oligonucleotides Via Phosphoramidite Derivatives", *Tetrahedron*, 49(10):1925–1963 (1993).
Horndler and Pfleiderer, *Heletica Chimica Acta*, 79:718–726 (May 8, 1996).

* cited by examiner

Primary Examiner—Richard L. Raymond
Assistant Examiner—Sudhaker B. Patel
(74) Attorney, Agent, or Firm—Drinker Biddle & Reath LLP

(57) ABSTRACT

Antiviral compounds and the water-soluble salts thereof have formula (I), wherein n is from 1 to 8; $R_1$ is selected from the group consisting of (a), wherein m is zero, 1, 2 or 3; and (b), wherein q is from 1 to 20; $R_2$ is independently selected from the group consisting of oxygen and sulfur; $R_3$ is independently selected from the group consisting of hydrogen and hydroxyl; and $R_4$ is selected from the group consisting of hydrogen, hydroxyl and (b); $R_5$ is selected from the group consisting of hydroxyl and (b); $R_6$ is selected from the group consisting of (c), (d) et (e), wherein x is from 1 to 20; provided that one of $R_1$, $R_4$ and $R_5$ is (b) wherein $R_6$ is defined as above; or water soluble salt thereof.

23 Claims, No Drawings

AMINOAKLANOYL-LINKED CONJUGATES OF 2',5'-OLIGOADENYLATE AND ANTIVIRAL USES THEREOF

CROSS-REFERENCE TO RELATED APPLICATIONS

This application claims the benefit of U.S. provisional application Ser. No. 60/049,745, filed Jun. 12, 1997 and U.S. provisional application Ser. No. 60/052,043, filed Jul. 9, 1997.

FIELD OF THE INVENTION

This invention relates to synthetic analogues of naturally occurring antiviral 2',5'-oligoadenylates wherein the analogues are conjugated to a carrier molecule to enhance cellular uptake.

BACKGROUND OF THE INVENTION

It is well established that the natural antiviral pathways ubiquitous in mammalian cells—the (2-5')oligo(A) synthetase/RNase L cascade and the PKR antiviral pathway—are activated on virus infections, including HIV-1 [2-5]. Both pathways require dsRNA, which on the one hand activates (2'-5')oligo(A) synthetase converting ATP into 2'-5'-linked oligoadenylates ("2-5A") with a 5'-terminal triphosphate function. These unusual oligonucleotides bind and activate RNase L leading to the degradation of viral RNA and subsequent inhibition of protein synthesis [3][4]. On the other hand, dsRNA-dependent PKR (p68 kinase) undergoes autophosphorylation and catalyzes phosphorylation of the α-submit of eIF-2, thereby inhibiting initiation of protein synthesis [6]. Although, (2'-5')oligoadenylates are rapidly inactivated by two different nucleases, the (2'-5') oligo(A)system represents a chemotherapeutic possibility for the control of virus and cell growth.

Many (2'-5')oligo(A)derivatives have been synthesized with the aim to increase biological activity and to avoid premature decomposition of the antivirally active substance. One of the modified (2'-5')oligo(A)analogues is the cordycepin-trimer core (2'-5')d³(A-A-A) [7][8]; U.S. Pat. No. 4,464,359 which was found to be biologically active, metabolically stable, and not toxic to cells [9]. Although, the trimer-cordycepin core effects no activation of RNase L [10]; this substance inhibits HIV-1 production [11] probably by weakening the complex formation of primer tRNA$^{Lys,3}$ to HIV-1 reverse transcriptase [5][12][13].

One of the major problems in application of oligonucleotides to cells and biological systems is their polyanionic structure which renders them difficult to penetrate cell membranes. Numerous efforts have been made to improve the cellular uptake of oligonucleotides, e.g., incorporation in liposomes [14] or syntheses of lipophilic conjugates [15–17]. The attachment of cholesterol, various vitamins, and lipids to the 2'-O- and 5'-O-position of the sugar moiety of monomeric and trimeric cordycepin has been described [18–20].

SUMMARY OF THE INVENTION

Compounds of the following formula are provided, useful in treating viral infection in plants and animals:

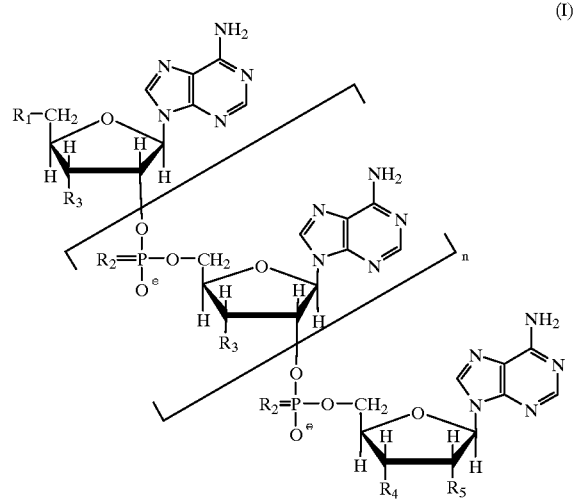

wherein:

n is from 1 to 8, preferably 1, 2 or 3, most preferably 1 or 2;

$R_1$ is selected from the group consisting of

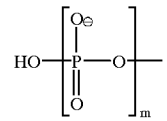

wherein m is zero, 1, 2, or 3; and

wherein q is from 1 to 20, preferably from 2 to 8, most preferably from 3 to 7;

$R_2$ is independently selected from the group consisting of oxygen and sulfur;

$R_3$ is independently selected from the group consisting of hydrogen and hydroxyl; and $R_4$ is selected from the group consisting of hydrogen, hydroxyl and

$R_5$ is selected from the group consisting of hydroxyl and

$R_6$ is selected from the group consisting of

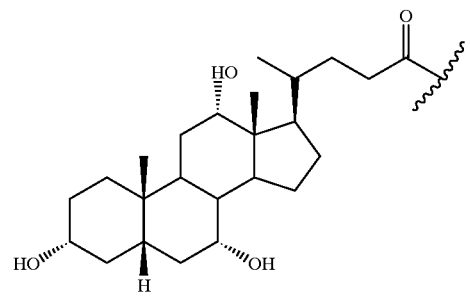

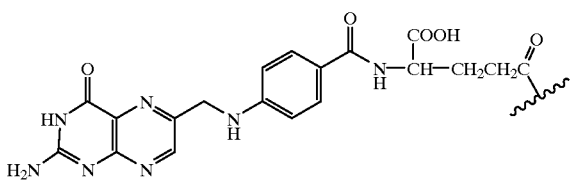

and

wherein x is from 1 to 20, preferably from 2 to 16, most preferably 10 to 14;
provided that one of $R_1$, $R_4$ and $R_5$ is

wherein $R_6$ is defined as above;
or water soluble salt thereof.

Preferably, the compounds of the invention include at least one nucleotide residue which is cordycepyl, that is, either $R_4$ is hydrogen or at least one of $R_3$ hydrogen. Most preferably, the compounds of the present invention comprise conjugates of 2',5'-oligocordycepin wherein the internucleotide linkages comprise phosphodiester groups, that is, all $R_2$ are oxygen, $R_4$ is hydrogen, and all $R_3$ are hydrogen.

The invention also comprises a method of treating viral infection in mammals or plants by administering an antivirally effective amount of a compound according to the above formula, or a water-soluble salt thereof. The invention also comprises an antiviral composition comprising such a compound or water soluble salt in combination with an agricultural carrier or pharmaceutical carrier.

Compounds of the invention include, for example, the following compounds, the 5'-mono-, di-, and triphosphates thereof, and water-soluble salts of any of them:

3'-deoxyadenylyl-(2'-5')-3'-deoxyadenylyl-(2'-5')-3'-deoxy-2'-O-[6-(tetradecanoylamino)-hexanoyl]adenosine;

3'-deoxyadenylyl-(2',5')-3'-deoxyadenylyl-(2'–5')-3'-deoxy-2'-O-{-[(3α,7α, 12α-trihydroxy-5β-cholan-24-oyl)-amino]hexanoyl}adenosine;

3'-deoxyadenylyl-(2'-5')-3'-deoxyadenylyl-(2'-5')-2'-O-{6-{{N-{4-{[(2-amino-1,4-dihydro-4-oxopteridin-6-yl)methyl]amino}benzoyl}-L-γ-glutanyl}amino}hexanoyl}-3'deoxy]adenosine;

Compounds of the invention further include, for example, the following compounds, and water-soluble salts thereof:

3'-deoxy-5'-O-[6-(tetradecanoylamino)hexanoyl]adenylyl-(2'-5')-3'-deoxyadenylyl-(2'-5')-3'-deoxyadenosine;

3'-deoxy-5'-O-{6-[(3α, 7α, 12α-trihydroxy-5β-cholan-24-oyl)amino]hexanoyl}adenylyl-(2'-5')-3'-deoxyadenylyl-(2'–5')-3'-deoxyadenosine; and 5'-O-{6-{{N-{4-{[(2-amino-[,4-dihydro-4-oxopteridin-6-yl)methyl]amino}benzoyl}-L-γ-glutanyl}amino}hexanoyl}-adenylyl-(2'-5')-3'-deoxyadenylyl-(2'-5')-3'-deoxyadenosine.

DETAILED DESCRIPTION OF THE INVENTION

According to the present invention, an aminoalkanoyl linkage serves as a biodegradable ester-bound spacer between a 2'-5'-oligoadenylate molecule, or derivative thereof, and a ligand which promotes cellular uptake. The spacer is cleaved by intercellular esterases, thereby releasing the oligomer from the ligand.

The 2'-5A derivative conjugates of Formula I may be prepared by attaching one of the following three cell uptake-promoting moieties cholanoyl:

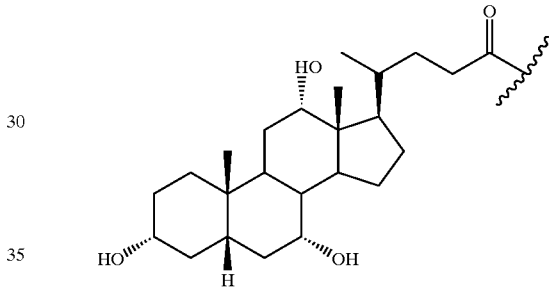

folanyl:

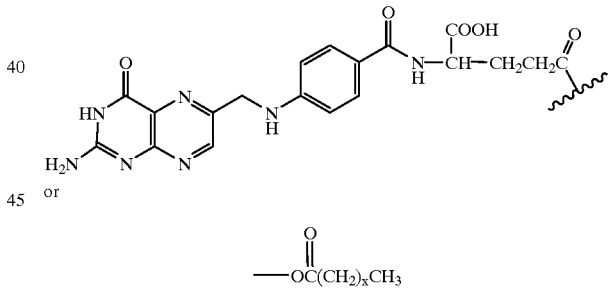

or

via the aminoalkanoyl spacer

—OC(CH₂)qNH— to the 2'-or 5'-terminal nucleoside of a 2',5'-phosphodiester, 2',5'-phosphorothioate or a 2',5'-mixed phosphorothioate/phosphodiester oligonucleotide.

The preparation of the 2',5'-phosphorothioates, including fully resolved enantiomers thereof, is disclosed in U.S. Pat. No. 4,924,624 and is incorporated herein by reference. The substitution of sulfur for oxygen in the 2',5'-phosphodiester backbone referenced above, introduces chirality into the molecules and introduces a new chemistry of the backbone. The core 2',5'-phosphorothioates exhibit increased resistance to phosphodiesterase and phosphatases and new biological activities compared to authentic 2–5A cores. A mixture of phosphorothioate and phosphodiester linkages is possible in the same oligomer, providing molecules with a mixed phosphodiester/phosphorothioate backbone, as described in PCT/US95/10683, the entire disclosure of which is incorporated by reference.

While the preparation and examples that follow are directed to conjugates of oligocordycepin derivatives, the conjugation described is equally applicable to the manufacture of oligomers comprising a chain of adenosine residues, or a mixed chain of cordycepin and adenosine residues as described in U.S. Pat. No. 4,859,768, the entire disclosure of which is incorporated by reference.

Chemical Synthesis

The synthesis of cordycepin [21], its protected derivatives 4 and 5[8], and the cordycepin-trimer derivative 27[20] have already been described in the literature. For the protection of the spacer, 6-aminohexanoic acid (1) was blocked at the amino function by reaction with N-{[(9H-fluoren-9-yl)methoxy]carbonyl}oxysuccinimide (2) in a 9% aqueous $Na_2CO_3$ solution and DMF to give compound 3 in 78% yield (Scheme 1). Esterification of the cordycepin derivatives 4 and 5 with 3 worked well with the carbodiimide method applying N-[3-(dimethylamino)propyl]-N-ethylcarbodiimide hydrochloride (EDC) and 4-(dimethylamino)pyridine (DMAP) as condensing agents to form the monomeric educts 6 and 7 in 90 and 80% yield, respectively. The 2'-O-conjugates 8 and 9 were prepared first by cleavage of the (9H-fluoren-9-yl)methoxycarbonyl (fmoc) protecting group from 6 with 3% piperidine in dry DMF, followed by acylation with myristic and cholic acid, respectively, in the presence of O-{[cyano(ethoxycarbonyl)-methyliden]-amino}-1,1,3,3-tetramethyluronium tetrafluoroborate (TOTU) and N-methylmorpholine. Detritiylation to 10 and 11 proceeded in good yields (88 and 87%), and subsequent elimination of the [2-(4-nitrophenyl)ethoxy[carbonyl (npeoc) group resulted in 86% yield of the myristic-acid conjugate 12 and in 78% yield of the cholic-acid conjugate 13. The structural analogues conjugated at 5'-O-position were synthesized in a similar manner first by deblocking the amino function in compound 7 and then by TOTU-activated amidation with myristic and cholic acid, respectively, to give 14 in 70% and 15 in 76% yield. Deprotection with 1,8-diazabicylo[5.4.0]undec-7-ene (DBU) gave 16 in 86% and 17 in 67% yield, respectively.

Scheme 1

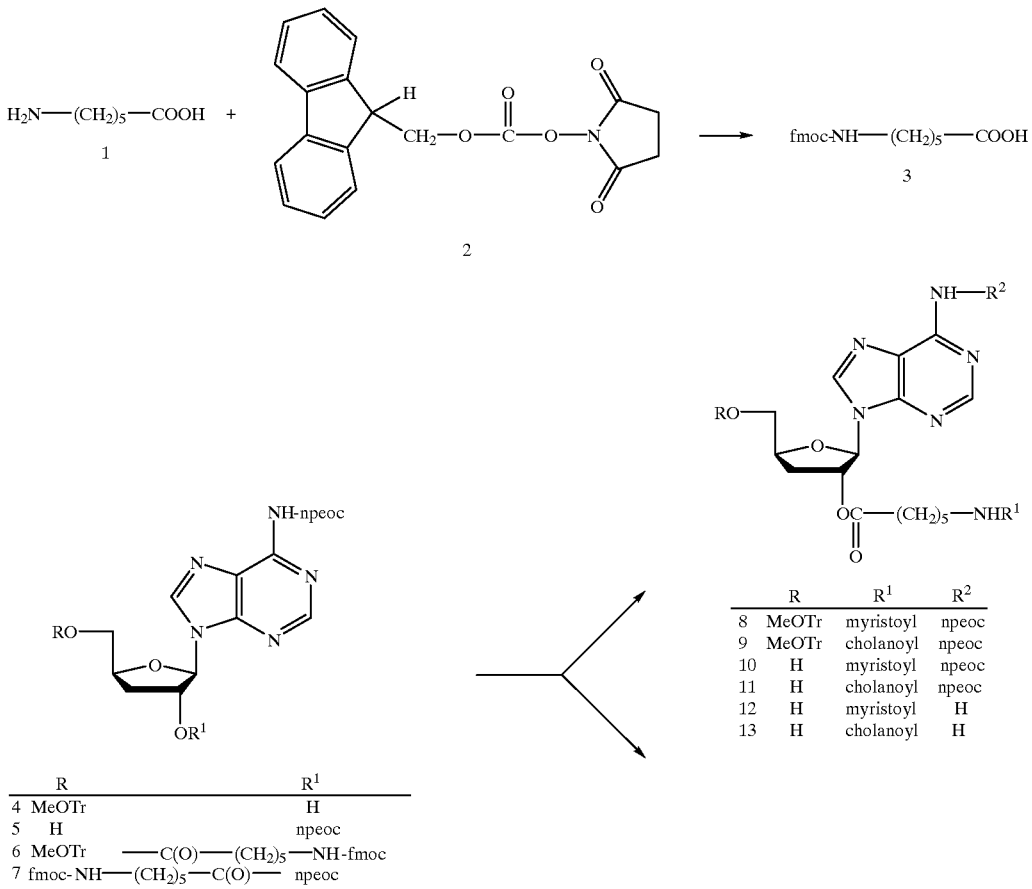

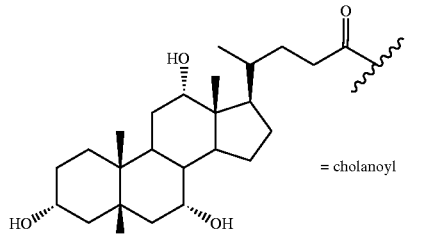
= cholanoyl

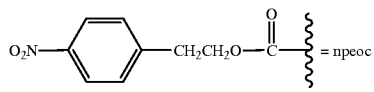
= npeoc

MeOTr = monomethoxytrityl   fmoc = (9H-fluoren-9-yl)methoxycarbonyl

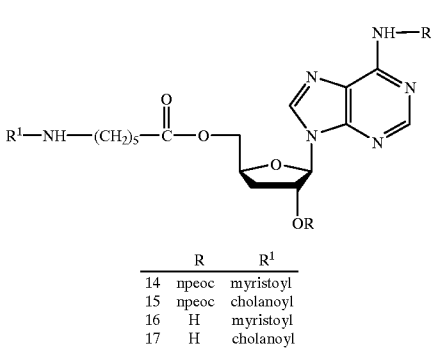

| | R | R¹ |
|---|---|---|
| 14 | npeoc | myristoyl |
| 15 | npeoc | cholanoyl |
| 16 | H | myristoyl |
| 17 | H | cholanoyl |

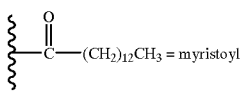
= myristoyl

Starting material for the trimeric 2'-O-conjugates was compound 18, which was prepared by acid treatment of 6. Stepwise condensation with 3'-deoxy-5'-O-(monomethoxytrityl)-N⁶[2-(4-nitrophenyl)ethoxycarbonyl]adenosine 2'-[2-(4-nitrophenyl)ethyl diisopropylphosphoramidite] [22] gave, on subsequent oxidation of the intermediary phosphite triester, the fully protected dimer 19 in 89% yield (Scheme 2). Quantitative detritylation to the dimer 20 and further condensation and oxidation generated the trimer 21 in 94% yield. Similarly to the one-pot reaction of the monomers, the fmoc group in compound 21 was cleaved off by treatment with 3% piperidine in dry DMF, and subsequent reaction with myristic or cholic acid by TOTU activation proceeded to the fully protected trimer conjugates 22 and 23 in 73 and 69% yield, respectively. Treatment with 2% TsOH in $CH_2Cl_2$/MeOH 4:1 and further β-elimination of the npe/npeoc groups with DBU in dry pyridine gave the desired cordycepin-trimer conjugates 24 (78%) and 25 (80%).

Scheme 2

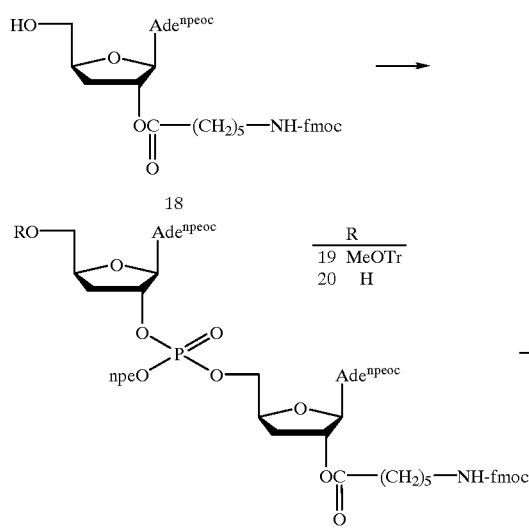

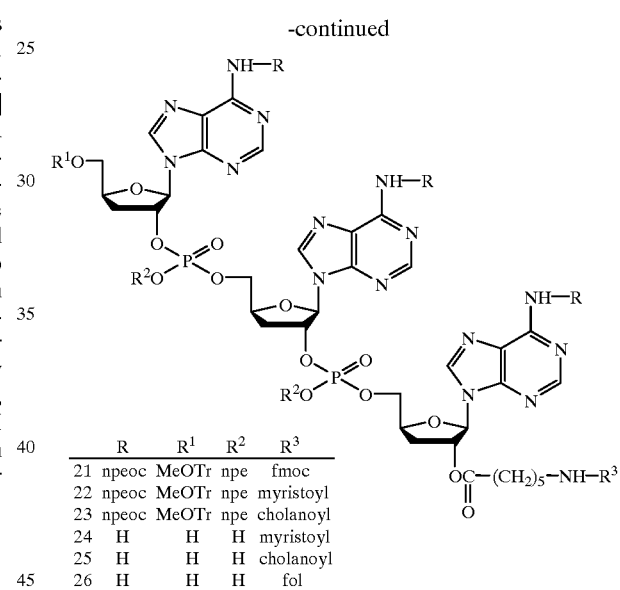

| | R | R¹ | R² | R³ |
|---|---|---|---|---|
| 21 | npeoc | MeOTr | npe | fmoc |
| 22 | npeoc | MeOTr | npe | myristoyl |
| 23 | npeoc | MeOTr | npe | cholanoyl |
| 24 | H | H | H | myristoyl |
| 25 | H | H | H | cholanoyl |
| 26 | H | H | H | fol |

Synthesis of the corresponding 5'-O-conjugates of cordycepin trimer was achieved by carbodiimide-activated esterification of the trimeric educt 27[20] with the fmoc-protected amino acid 3 to give compound 28 in 79% yield (Scheme 3). Subsequent deblocking of the amino group and acylation with myristic and cholic acid gave conjugates 29 and 30 in 69 and 75% yield, respectively. β-Elimination of the npe and npeoc groups by DBU treatment generated the deblocked cordycepin-trimer 5'-O-conjugates 31 and 32 in 95 and 96% yield, respectively.

Scheme 3

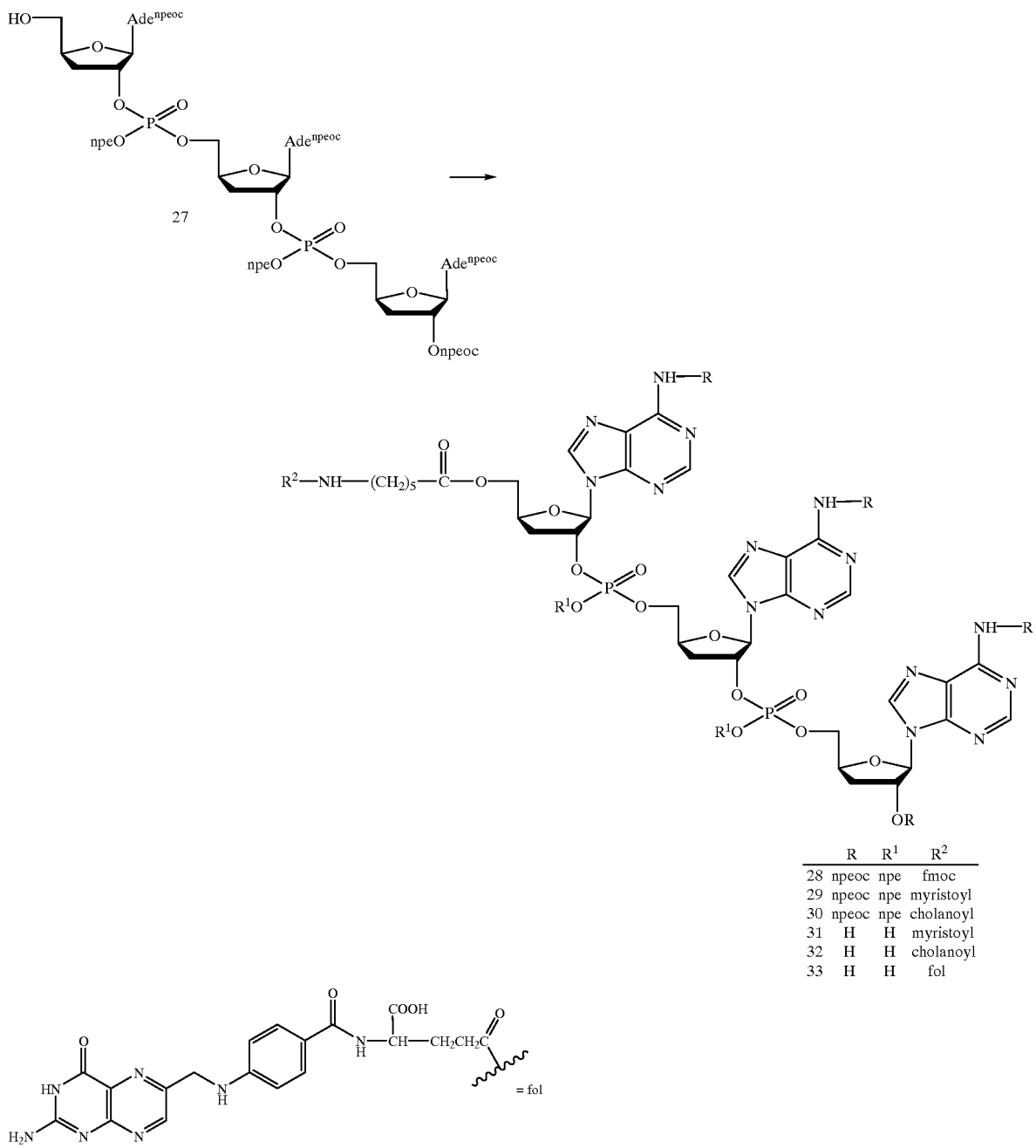

|    | R     | R¹  | R²        |
|----|-------|-----|-----------|
| 28 | npeoc | npe | fmoc      |
| 29 | npeoc | npe | myristoyl |
| 30 | npeoc | npe | cholanoyl |
| 31 | H     | H   | myristoyl |
| 32 | H     | H   | cholanoyl |
| 33 | H     | H   | fol       |

The approach to the folic-acid conjugates 26 and 33 did not allow to isolate the intermediary products due to their unusual and inconvenient physical properties. Both trimeric educts, compound 21 and 28, respectively, were treated in the first step with 3% piperidine in dry DMF and then successively condensed with 6 equiv. of EDC-activated folic acid. After evaporation, the crude product was treated with $Et_2O$ and $CH_2Cl_2$ and then deprotected by DBU in dry pyridine. Finally, the mixture was neutralized with AcOH and evaporated, and the residue treated with MeCN, and subsequently with 80% $AcOH/H_2O$, and centrifuged. The supernatant was evaporated and submitted to final HPLC purification providing the desired conjugates 26 and 33 in relatively low yields.

Biological Utility

The compounds of the present invention may be combined with appropriate pharmaceutical or agricultural carriers to form an antiviral composition.

For pharmaceutical use, the compounds of the invention may be taken up in pharmaceutically acceptable carriers, such as, solutions, suspensions, tablets, capsules, ointments, elixirs and injectable composition and the like. They are administered to subjects suffering from viral infection. The dosage administered depends upon the nature and severity of the infection, the disease stage, and, when administered systematically, the size and weight of the infected subject.

The compounds are generally administered in the form of water-soluble salts. Pharmaceutically acceptable water soluble salts include, for example, the sodium, potassium or ammonium salts of the active compounds. They are readily dissolved in water or saline solution. Thus, the preferred formulation for pharmacological use comprises a saline solution of the desired compound in salt form. The formulation may further contain an agent, such as a sugar or protein, to maintain osmotic balance. The salt form of the compound is preferred owing to the relatively high acidity (about pH 3) of the acid form of the compounds.

The compounds of the invention may be used as a treatment for humans and animals from viral infectives such as Herpes simplex, rhinovirus, hepatitis and other infections of the hepatitis virus family, Epstein Barr virus, measles virus, multiple sclerosis (which may be caused by a viral agent) and the various Human Immunodeficiency Viruses ("HIV"), such as HIV-1, which causes cutaneous T cell lymphoma, HIV-2, which causes Sezary lymphoma, and HIV-3, which is responsible for Acquired Immune Deficiency Syndrome ("AIDS"). The compounds of the invention inhibit HIV-1 induced syncytia formation.

The compounds may be applied topically to treat skin cancers caused by radiation, carcinogens or viral agents. Such skin cancers include cutaneous T-cell lymphoma, Sezary lymphoma, Xeroderma pigmentosium, ataxia telangiectasia and Bloom's syndrome. A sufficient amount of a preparation containing a compound of the invention is applied to cover the lesion or affected area. An effective concentration of active agent is between about $10^{-3}$ M and $10^{-5}$ M, with $10^{-4}$ M being preferred.

The compounds of the present invention may also be used to treat plant-infecting virus, particularly tobacco mosaic virus, and other viruses which cause necrosis in turnips, cucumbers, orchids and in other plants. Such viruses include, but are not limited to, tobacco vein mottling virus, vesicular stomatitis virus, vaccinia virus, turnip necrosis virus, and cymbidium orchid virus.

The compounds may be administered effectively to plants by topical application by abrasion of the leaf surface, aerosol spray, treatment of the soil, spraying, or dusting.

An effective antiviral composition may be formed by combining one or more of the compounds of the invention with a carrier material suitable for agricultural use. The active compound may also be administered by spraying insect vectors such as aphids, thrips and whiteflies which carry virus to plants. The dosage administered depends upon the severity of the infection.

The compounds of the invention may be applied to plant seeds prior to germination to control viruses contained in the germ plasm. The seeds may be soaked in a solution of polyethylene glycol ("PEG") containing one or more of the compounds. PEG brings the seeds to physiological activity and arrest. The relative concentration of active compound to PEG depends upon the type of seed under treatment.

Plants may be effectively treated with an aqueous formulation containing from about $10^{-1}$ to about $10^{-2}$ M concentration of active ingredient. The compounds of the invention may be applied at very low concentrations. An effective amount of active ingredient on the plant surface is from about $10^{-8}$ to about $10^{-12}$ mole per $cm^2$ of plant surface area, with about $10^{-10}$ mole to about $10^{-12}$ mole per $cm^2$ being preferred. For the typical tobacco plant, $10^{-5}$ M of compound is effective. At this rate, one pound of active ingredient is sufficient to treat $2 \times 10^{-8}$ tobacco plants.

For agricultural application, the compounds are advantageously administered in the form of water-soluble salts, e.g. ammonium or potassium salts. Sodium salts are generally avoided in treating edible plants.

The compounds of the invention are readily dissolved in water, particularly at such low concentrations. Aqueous formulations for agricultural use may optionally contain a sticker and/or a UV-stabilizer. Such agents are well-known to those skilled in the art. Fatty acids (1%) are useful as spreader sticker agents. Effective UV-stabilizers include, for example, p-aminobenzoic acid.

For antiviral use in mammals, the compounds of the invention are administered parenterally, such as intravenously, intraarterially, intramuscularly, subcutaneously or when administered as an anti-cancer agent, intratumorally. The preferred route of administration for antiviral therapy is intravenous injection. The compounds of the invention may be administered to mammals at very low concentrations. The actual dosage administered may take into account the size and weight of the patient, whether the nature of the treatment is prophylactic or therapeutic in nature, the age, health and sex of the patient, the route of administration, the nature and stage of the affliction, and other factors. An effective daily dosage of active ingredient, based upon in vivo studies involving other 2–5A analogues, is from about 0.25 g per 70 kg of body weight (approximately 152 lbs) to about 2.5 g per 70 kg of body weight. The preferred daily dosage is about 0.5 g per 70 kg of body weight. Those skilled in the art should readily be able to derive appropriate dosages and schedules of administration to suit the specific circumstance and needs of the patient.

It is expected that an effective treatment regimen includes administration of the daily dosage for two days. Treatment is continued at least until the disease condition is substantially abated.

Preferably, the therapeutic end point is determined by testing for the continued presence of viral DNA. Such testing can be done by polymerase chain reaction (PCR) in which the presence of viral DNA is assayed according to conventional PCR. PCR primers of appropriate nucleotide sequences for amplification of viral DNA can be prepared from known viral nucleotide sequences. To obtain DNA for testing, patient peripheral blood mononuclear cells are lysed with an appropriate lysing agent, such as NP-40.

Alternatively, testing for the continued presence of the virus can be performed by an antigen-antibody assay using any of the known monoclonal or polyclonal antisera against a protein antigen of the target virus protein coat. For example, an antigen-antibody assay may be employed to detect any of the protein antigen in the virus HIV protein coat, for example, the gp120, p17 or p24. Moreover, the target antigen is not limited merely to coat protein antigens. Antisera can be targeted against a suitable non-coat protein antigen, such as the HIV reverse transcriptase (RT) molecule. Monoclonal antibodies to HIV RT are known. Sobol et al., *Biochemistry* 1991, 30, 10623.

Additionally, testing for the presence of the infecting virus during or post-treatment could be accomplished by an assay which assesses the viral load in the patient's blood stream. This can be done by determining syncytia formation. See procedure outlined in Henderson et al., *Virology*, 1991, 182, 186.

In addition to administration with conventional carriers, the compounds of the present invention may be administered by a variety of specialized oligonucleotide or nucleic acid delivery techniques. 2–5A and its analogues have been successfully encapsulated in various encapsulating materials, such as in unilamellar liposomes and delivered with the aid of monoclonal antibodies to cells, Bayard et al., Eur. J. Biochem., 1985, 151, 319. Reconstituted Sendai virus envelopes have been successfully used to deliver RNA and DNA to cells, Arad et al., Biochem. Biophys. Acta. 1986, 859, 88. Moreover, the virus envelope is not limited to Sendai virus, but could include encapsulation in any retroviral amphotrophic particle. For example, an HIV envelope could be formed from any part or all of the outer protein coat of a non-infectious HIV particle. Such particles as gp 120 can be cloned by known recombinant techniques. These techniques may be utilized for introduction of the present 2–5A oligoadenylate derivatives into cells.

Biological Studies

Three studies were performed to determine the antiviral activity of the (2'-5')oligonucleotide derivatives of the present invention: (i) inhibition of HIV-1-replication, (ii) inhibition of HIV-1 reverse-transcriptase (RT) activity, and (iii) activation of recombinant human GST-RNase L. The concentration of compound in the replication and RT assays was 300 $\mu$M, and 10$\mu$M in the GST-RNase L activation assay. The compounds tested were the cordycepin trimer folate conjugates 26 and 33. Cordycepin and the 2',5'-cordycepin trimer core ("CCC") were also tested for comparison.

Inhibition of HIV-1 Replication

The infected centers assay as described by Henderson et al., Virology 1991, 182, 186, was used to measure the ability of the conjugated trimer core compounds of the invention to inhibit HIV-1 induced syncytia formation, an indicator of HIV-1 replication in T cells. Freshly isolated peripheral blood lymphocytes (PBL) were treated with cordycepin trimer core-folate conjugate 26 or 33 (300 $\mu$M) for 2 hours and infected with HIV-1 strain IIIB at a multiplicity of infection of approximately 0.1. The infected PBL were maintained in RPMI-1640 medium supplemented with 10% (v/v) heat-inactivated fetal calf serum at 37° C. in a humidified 5% $CO_2$ in air atmosphere. After 48 hours, the cells were washed twice in Hank's balanced salt solution, serially diluted and seeded into multiple wells of a 96-well microtiter plate. Immediately, 2×105 exponentially growing Sup T1 cells were added to each well; Sup T1 cells readily form a syncytium with a cell which is productively infected with HIV-1. The wells were examined daily for the presence of syncytia, using a tissue culture microscope. The first signs of syncytia formation can be seen in 12 hours, with some complete syncytia developing by 24 hours. Final results were read at 72 hours. Each syncytium was counted as a single infected cell. The number of syncytia per seeded cell was determined and expressed as an infected center per infected cell. The number of syncytia per 104 cells was 144 for the control Sup T1 cells. The data is shown in Table 1. The mean of triplicate determinations is shown; variance did not exceed 5–10%.

Inhibition of HIV-1 Reverse-Transcriptase Activity

Sup T1 cells were treated with cordycepin trimer core-folate conjugate 26 or 33 (300 $\mu$M) for 6 hours and then infected with HIV-1 at a multiplicity of infection of approximately 0.1. At 96 hours post-infection, culture supernatant was removed and HIV-1 RT activity was assayed in triplicate as described by Henderson et al., Virology 1991, 182, 186. Briefly in this method, 25 $\mu$l of culture supernatant was added to a 50 $\mu$l cocktail containing 50 mM Tris (pH 8.0), 20 mM dithiothreitol, 10 mM $MgCl_2$, 60 mM NaCl, 0.05% Nonidet p-40, 5 $\mu$g/ml oligodeoxythymidylic acid, 10 $\mu$g/ml polyriboadenylic acid, 10 $\mu$M deoxythymidine triphosphate and 1mCi [$\alpha^{32}$P]thymidine 5'-triphosphate. The mixture was incubated at 37° C. for 2 hours. Fifty microliters of the cocktail were then spotted onto diethylaminoethyl (DEAE) paper, dried, washed with 2× SSC solution (three times for 10 minutes each time) and 95% ethanol (two times for 5 minutes each time), dried and exposed to radiographic film for 18 to 24 hours at −80° C. The filters were cut and final quantitation was determined by scintillation spectrometry.

The data for the HIV-1 RT activity is shown in Table 1 as a percent of RT activity. Control values for RT activity ranged from 24,000 to 33,000 dpm [$^{32}$p] incorporated. The mean of duplicate determinations is shown in Table 1. Variance did not exceed 5–10%.

Activation of Recombinant Human GST-RNase L

Human recombinant RNase L was expressed in E. coli (DH5$\alpha$) as a fusion protein of glutathione-S-transferase (GST). Activation of human recombinant GST-RNase L was measured as the percent of poly(U)[$^{32}$P]pCp hydrolyzed in the presence of cordycepin trimer core-folate conjugate 26 or 33 (10 $\mu$M) as described by Sobol et al., J. Biol. Chem. 1995, 270, 5963. The data is shown in Table 1 as the mean of duplicate determinations. Variance did not exceed 5–10%.

TABLE 1

Results of Biological Studies
Inhibition of HIV-1-Replication and Biological Activities of Cordycepin Trimer Core-Folate Conjugates 26 and 33

|  | Inhibition of syncytia formation[a] fold | Inhibition of HIV-1 RT activity[b] (%) | Activation of RNase L[c] (%) |
|---|---|---|---|
| 26 CCC-2'-suc-Fol | 2.4 | 45 | 0 |
| 33 5'-Fol-suc-CCC | 7.2 | 81 | 35 |
| CCC | 4.8 | 96 | 12 |
| Cordycepin | 1.5 | 13 | NT[d] |

[a]Inhibition of HIV-1 replication was determined by HIV-1 induced syncytia formation (fold reduction in infection) for each cordycepin-trimer folate derivative of 2-5A (300 $\mu$M). The number of syncytia/$10^4$ cells was 144 for the control Sup T1 cells. The mean of triplicate determinations is shown; variance did not exceed 5–10%.
[b]Percent inhibition of HIV-1 reverse transcriptase (HIV-1 RT) activity was measured for each cordycepin-trimer folate derivative of 2-5A at 300 $\mu$M. Control values for HIV-1 RT activity ranged from 24,000 to 33,000 dpm incorporated. The mean of duplicate determinations is shown; variance did not exceed 5–10%.
[c]The activation of recombinant human RNase L was measured as the percent hydrolysis of poly(U)-3'-[$^{32}$P]pCp in the presence of the cordycepin-trimer folate derivative of 2-5A (10 $\mu$M). The mean of a duplicate determination is shown; variance did not exceed 5–10%.
[d]Not tested.

Inhibition of HIV-1 RT activity with 26 and 33 was 45 and 81%, respectively, compared to 96 and 13% inhibition of HIV-1 RT activity by the 2'-5'-oligocordycepin trimer core and cordycepin, respectively. When folic acid is covalently linked to C(2') at the 2'-terminus of the cordycepin trimer core as in 26, GST-RNase L is not activated; however, covalent linkage to C(5') at the 5'-terminus as in 33 activates GST-RNase L by 35%. These data suggest that the inhibition of HIV-1 replication by 26 is due to inhibition of HIV-1 RT. However, the 7.5-fold reduction in syncytia formation by 33 is in part attributed to the inhibition of HIV-1 RT activity and the activation of RNase L.

Chemical Synthesis of Core Conjugates

The synthesis of the unphosphorlyated compounds of the present invention is illustrated by the following non-limiting examples.

General. TLC: Precoated silica gel TLC sheets F1500 LS 254 from Schleicher & Schüll. Prep. TLC: silica gel 60 $PF_{254}$ (Merck). Prep. column flash chromatography (FC): silica gel for flash chromatography (Baker). HPLC: Merck-Hitachi L-6200, L-3000 photo diode array; detector; column RP18. 125×4 mm, 5 µm, Merck; flow rate 1 ml/min. UV/VIS: Perkin Elmer Lambda 5;$\lambda_{max}$ in nm (log ε). $^1$H-NMR: Bruker AC 250, δ in ppm rel. to DMSO.

Preparation 1

6-{{[(9H-Fluoren-9-yl)methoxy]carbonyl}amino}hexanoic Acid (3).

To a solution ("soln.") of 6-aminohexanoic acid (1; 144 mg, 1.1 mmol) in 9% aq. $Na_2CO_3$ soln. (2.4 ml) was added a soln. of (9H-fluoren-9-yl)methyl succinimidyl carbonate (2; 337 mg, 1 mmol) in DMF (2.5 ml). After stirring for 1 h at room temperature ("r.t."), the mixture was diluted with $H_2O$ (50 ml) and extracted twice with $Et_2O$ (2×20 ml). Then, the $H_2O$ phase was acified with conc. HCl soln. to pH 2 and extracted with AcOEt (5×30 ml). The organic ("org.") layer was dried ($MgSO_4$) and evaporated. The residue was crystallized in $CHCl_3$/petroleum ether: 306 mg (86%) of 3. Colorless crystals. M.p. 116°. $^1$H-NMR ($CDCl_3$): 7.80–7.55 (2m, H—C(1)(fmoc), H—C(4)(fmoc), H—C(5)fmoc, H—C(8)(fmoc); 7.45–7.25 (m, H—C(2)(fmoc), H—C(3)(fmoc), H—C(6)(fmoc), H—C(7)(fmoc); 4.45 (m, $CH_2O$(fmoc)); 4.2(m, H—C(9)(fmoc)); 3.25–3.0, 2.4, 1.8–1.3 (3m, $NH(CH_2)_5CO$). Anal. calc. for $C_{21}H_{23}NO_4$ (353.42): C 71.37, H 6.56, N 3.96; found: C 71.35, H 6.65, N 3.93.

Preparation 2

3'-Deoxy-2'-O-{6-{{[(9H-fluoren-9-yl) methoxy]carbonyl}amino}hexanoyl}-5'-O-(monomethoxytrityl)-$N^6$-[2-(4-nitrophenyl)ethoxycarbonylladenosine (6).

A mixture of 3'-deoxy-5'-O-(monomethoxytrityl)-$N^6$-[2-(4-nitrophenyl)ethoxycarbonyl]adenosine (4; 215 mg, 0.3 mmol) [8], 3 (120 mg, 0.3 mmol), N-[3-(dimethylamino)propyl]-N'-ethylcarbodiimide hydrochloride (EDC; 58 mg, 0.3 mmol), and 4-(dimethylamino)pyridine (DMAP; 37 mg, 0.3 mmol) in dry $CH_2Cl_2$ (4 ml) was stirred at r.t. for 3 h, diluted with $CH_2Cl_2$ (60 ml), and washed with sat. $NaHCO_3$/$NaCO_3$ soln. (25 ml). The aqueous ("aq.") phase was reextracted with $CH_2Cl_2$ (40 ml), the combined org. layer extracted with 10% citric acid soln., the acid phase reextracted with $CH_2Cl_2$, the combined org. layer dried ($MgSO_4$) and evaporated, and the residue purified by FC (silica gel, 14.5×2 cm, toluene/AcOEt 1:1 then 1:1+3% MeOH): 292 mg (ca. 93%) of 6 which was already contaminated with amino acid. A pure sample of 6, was obtained by prep. TLC (silica gel, 20×40 cm, $CHCl_3$+4% MeOH) of 138 mg of the crude product: 117 mg of 6. UV ($CH_2Cl_2$): 300 (4.00), 286 (sh, 4.14), 272 (sh, 4.63), 266 (4.66), 237 (sh, 4.36). $^1$H-NMR ($CDCl_3$): 8.61, 8.58, 8.17–8.13 (3s, d, H—C(8), H—C(2), NH, 2 H o to $NO_2$); 7.76–7.16 (m, 8 H of fmoc. 2 H m to $NO_2$, 12 H of MeOTr); 6.78 (d, 2 H o to MeO); 6.13 (d, H—C(1')); 5.73 (m, H—C(2')); 4.89–4.15 (m, $NH(CH_2)_5CO$), H'C(4'), $OCH_2CH_2$, H—C(9)(fmoc), $CH_2O$(fmoc)); 3.76 (s, MeO); 3.5–3.35 (m, 2H—C(5')); 3.35–3.15 (m, $OCH_2CH_2$, 1 $CH_2$ of $NH(CH_2)_5CO$); 2.65 (m, H—C(3')); 2.39 (t, 1 $CH_2$ of $NH(CH_2)_5CO$); 1.7–1.2 (m, 3 $CH_2$ of $NH(CH_2)_5CO$). Anal. calc. for $C_{60}H_{57}N_7O_{11}$ (1052.15): C 68.49, H 5.46, N 9.32; found: C 68.56, H 5.67, N 9.12.

Preparation 3

3'-Deoxy-5'-O-{6-{{[(9H-fluoren-9-yl)methoxy]carbonyl}amino}hexanyl}-$N^6$,2'-O-bis[2-(4-nitrophenyl)ethoxycarbonyl]adenosine (7).

As described in Preparation 2, with 3'-deoxy-$N^6$,2'-O-bis[2-(-nitrophenyl)ethoxy-carbonyl]adenosine (5; 1.912 g, 3 mmol) [8], 3 (1.166 g, 3.3 mmol), EDC (633 mg, 3.3 mmol), DMAP (403 mg, 3.3 mmol), and anh. $CH_2Cl_2$ (10 ml; 3.5 h). Workup with $CH_2Cl_2$ (150 ml), $NaHCO_3$ soln. and 10% citric acid soln. (80 ml) and purification by FC (silica gel. 7.5×4.5 cm, toluene/AcOEt 1: 1, then 1: 1+2% MeOH) gave 2.35 g (80%) of 7. Amorphous solid. UV ($CH_2CH_2$): 297 (4.12), 286 (sh, 4.31), 272 (sh, 4.66), 266 (4.71). $^1$H-NMR ($CDCl_3$): 9.3–8.0 (m, H—C(8), H—C(2), NH, 4 H o to $NO_2$); 7.75–7.3 (m, 8 H of fmoc, 4 H m to $NO_2$); 6.12(s, H—C(1')); 5.71 (m, H—C(2')); 5.18 (t, $NH(CH_2)_5CO$); 4.65–4.15 (m H—C(4'), 2 $OCH_2CH_2$, H—C(9)(fmoc), $CH_2O$(fmoc), 2 H—C(5')); 3.2–3.0 (m, 2 $OCH_2CH_2$, 1 $CH_2$ of $NH(CH_2)_5CO$); 2.65 (m, H—C(3')); 2.25 (m, H—C(3'), 1 $CH_2$ of $NH(CH_2)_5CO$); 1.65–1.15 (m, 3 $CH_2$ of $NH(CH_2)_5CO$). Anal. calc. for $C_{49}H_{48}N_8O_{14}$ (972.97): C 60.49, H 4.97, N 11.52; found: C 60.83, H 5.08, N 11.15.

Preparation 4

3'-Deoxy-5'-O-(monomethoxytrityl)-$N^6$-[2-(4-nitrophenyl)ethoxycarbonyl]-2'-O-[6-(tetradecanoylamino)hexanoyl]adenosine (8).

For acid activation, a mixture of tetradecanoic acid (128 mg, 0.56 mmol), TOTU (184 mg, 0.56 mmol), and N-methylmorpholine (57 mg, 0.56 mmol) in absolute ("abs.") DMF (4 ml) was kept at r.t. for 1.5 h. Then 6 (490 mg, 0.466 mmol) was treated with 3% piperidine in abs. DMF (7 ml; 10 min) and evaporated. The above-mentioned soln. was added and the mixture stirred for 3 h at r.t. and evaporated. The residue was diluted with AcOEt (180 ml), washed with NaHCO, soln. (2×80 ml), the aq. phase reextracted with AcOEt (80 ml), the combined org. layer dried ($MgSO_4$) and evaporated, and the residue purified by FC (silica gel, 11×2 cm, toluene/AcOEt 1:1+2% MeOH, 1: 1+3% MEOH): 408 mg (84%) of 8. Amorphous solid. UV($CH_2Cl_2$): 272 (sh, 4.39); 267 (4.44), 237 (sh, 4.30). $^1$H-NMR ($CDCl_3$): 8.38, 8.18 (2s, m, H—C(8), H—C(2), 2 H o to $NO_2$, NH(ade)); 7.45–7.20 (m, 2H m to $NO_2$, 12H of MeOTr); 6.79 (d, 2 H o to MeO); 6.14 (d, H—C(1')); 5.73 (m, H—C(2')): 5.50 (t, $NH(CH_2)_5CO$); 4.55 (m, t, H—C(4'), $OCH_2CH_2$); 3.78 (s, MeO); 3.41 (m, 2 H—C(5')); 3.20 (q, 1 $CH_2$ of $NH(CH_2)_5CO$); 3.15 (t, $OCH_2CH_2$); 2.6, 2.2 (2m, H—C(3')); 2.39, 2.14 (2m, 2 $CH_2$ of $NH(CH_2)_5CO$, 2 H of $Me(CH_2)_{12}CO$); 1.7–1.15 (m, 28 H 2 $CH_2$ of $NH(CH_2)_5CO$, $Me(CH_2)_{12}CO$); 0.87 (t,$Me(CH_2)_2CO$). Anal. calc. for $C_{59}H_{73}N_7O_{10}$½ $H_2O$ (1040.27): C 67.52, H 7.06, N 9.34; found: C 67.25, H 7.20, N 9.33.

Preparation 5

3'-Deoxy-5'-O-(monomethoxytrityl)-$N^6$-[2-(4-nitrophenyl)ethoxycarbonyl]-2'-O-{6-[(3α, 7α, 12α-trihydroxy-5β-cholan-24-oyl)aminolhexanoyl}adenosine (9).

As described in Preparation 4, with cholic acid (450 mg, 1.1 mmol) and TOTU (361 mg, 1.1 mmol) in abs. DMF (5 ml; 1h). Deblocking of 6 (1.052 g, 1 mmol) with 3% piperidine in abs. DMF (15 ml; 10 min) and addition of the above-mentioned soln. (r.t., 1.5 h). Workup with AcOEt (200 ml) and NaHCO$_3$ soln. (2×100 ml), reextraction, and purification by FC (silica gel, 14×3.5 cm, CHCl$_3$, then CHCl$_3$/MeOH 98:2, 96:4, 93:7, 90:10) gave 944 mg (77%) of 9. Amorphous solid. UV (CH$_2$Cl$_2$): 272 (sh, 4.42), 267 (4.47), 237 (sh, 4.31). $^1$H-NMR (CDCl$_3$): 9.12 (br., NH(ade)); 8.68–8.11 (2s, d, H—C(8), H—C(2), 2 H o to NO$_2$); 7.48–7.12 (m, 2 H m to NO$_2$, MeOTr); 6.8 (d, 2 H o to MeO); 6.1 (s, H—C(1')); 5.88 (t, NH(CH$_2$)$_5$CO); 5.63 (m, H—C(2')); 4.6 (m, H—C(4')); 4.51 (t, OCH$_2$CH$_2$); 3.98–3.7 (s, m, MeO, 2H of chol); 3.55–3.1 (m, 8H, 2H—C(5'), OCH$_2$CH$_2$, 1 CH$_2$ of NH(CH$_2$)$_5$C)$_1$ 2 H of chol.); 2.65–0.6 (m, 2H—C(3'), 4CH$_2$ of NH(CH$_2$)$_5$CO), 33 H of chol.). Anal. calc. for C$_{69}$H$_{85}$ N$_7$O$_{13}$ (1220.47): C 67.90, H 7.02, N 8.03; found C 67.74, H 7.26, N. 7.65

Preparation 6

3'-Deoxy-N$^6$-[2-(4-nitrophenyl)ethoxycarbonyl]-2 '-O-[6-(tetradecanoylamino)hexanoyl]adenosine (10).

Compound 8 (330 mg, 0.317 mmol) was stirred at r.t. in CH$_2$Cl$_2$/MeOH 4:1 (6 ml) containing 2% of TsOH.H$_2$O for 15 min. Then the mixture was diluted with CH$_2$Cl$_2$ (70 ml) and washed with sat. NaHCO$_3$ soln. (2×40 ml), the aq. phase reextracted with CH$_2$Cl$_2$, the combined org. layer dried (MgSO$_4$) and evaporated, and the residue purified by FC (silica gel, 12×2 cm, CHCl$_3$, CHCl$_3$+5% MeOH). The obtained oily substance was treated with small amounts of Et$_2$O/MeCN 2:1 to give 215 mg (88%) of 10. Amorphous solid. UV (CH$_2$Cl$_2$); 272 (sh, 4.36), 267 (4.41). $^1$H-NMR (CDCl$_3$):8.71, 8.21–8.15 (2m, H—C(8), H—C(2), 2 H o to NO$_2$,NH(ade)); 7.45 (d, 2 H m to NO$_2$); 6.03 (d, H—C(1')); 5.58 (m, H—C(2')); 5.55 (br., NH(CH$_2$)$_5$CO); 5.0 (br., OH—C(5')); 4.65–4.50 (m, t, H—C(4'), OCH$_2$CH$_2$); 4.12, 3,75 (2m, 2 H—C(5')); 3.25(q, 1 CH$_2$ of NH(CH$_2$)$_5$CO); 3.15 (t, OCH$_2$CH$_2$);2.9, 2.25 (2m, 2 H—C(3')); 2.35, 2.15 (2t, 2 CH$_2$ of NH(CH$_2$)$_5$CO), 2 H of Me(CH$_2$)$_{12}$CO); 1.7–1.15 (m, 28 H, 2 CH$_2$ of NH(CH$_2$)$_5$CO, Me(CH$_2$)$_{12}$CO); 0.87 (t, Me(CH$_2$)$_{12}$CO)$_{12}$ Anal. calc. for C$_{39}$H$_{57}$N$_7$O$_9$ ½ H$_2$O (782.02): C 59.90, H 7.41, N 12.54; found: C 60.27, H 7.66, N 12.06.

Preparation 7

3'-Deoxy-N$^6$-[2-(4-nitrophenyl)ethoxycarbonyl]-2'-O-{6-[(3α, 7α, 12α-trihydroxy-5β-cholan-24-oyl)amino]-hexanoyl}adenosine (11).

As described in Preparation 6, with 9 (860 mg, 0.705 mmol) and CH$_2$Cl$_2$/MeOH 4:1 (14 ml) containing 2% of TsOH H$_2$0 (15 min). Workup with CH$_2$Cl$_2$ (70 ml) and sat. NaHCO$_3$ soln. (2×40 ml), and reextraction, and purification by precipitation of the crude product in Et$_2$O (100 ml) gave 578 mg (87%) of 11. UV (MeOH): 272 (sh, 4.39), 267 (4.43). $^1$H-NMR (CDCl$_3$): 9.70 (s, NH(ade)); 8.73, 8.44 (2s, H—C(8)), H—C(2)); 8.17 (d, 2 H o to NO$_2$); 7.45 (d H m to NO$_2$); 6.18 (m, NH(CH$_2$)$_4$CO); 6.10 (d, H—C(1')); 5.57 (m, H—C(2')); 5.05 (br. OH—C(5')); 4.55–4.45 (m, H—C (4'), OCH$_2$CH$_2$); 4.1–3.65 (m, 2 H of chol., 2 H—C(5')); 3.5–2.7 (m, 4 H of chol., OCH$_2$CH$_2$, 1 CH$_2$ of NH(CH$_2$)$_5$CO), H—C(3')); 2.45–0.6 (m, H—C(3'), 4 CH$_2$ of NH(CH$_2$)$_5$CO), 33 H of chol.). Anal calc. for C$_{49}$H$_{69}$N$_7$O$_{12}$ (948.13): C 62.07, H 7.34, N 10.34; found: C 61.54, H 7.41, N 9.92.

Preparation 8

3'-Deoxy-2'-O-[6-(tetradecanoylamino)hexanoyl] adenosine (12).

Compound 10 (160 mg, 0.208 mol) was co-evaporated twice with abs. pyridine and then dissolved in abs. pyridine (2 ml). DBU (158 mg, 1.04 mmol) was added, the mixture kept at r.t. for 18 h, then AcOH (62 mg, 1.04 mmol) added, and the soln. evaporated. The residue was diluted with CHCl$_3$ (80 ml) and washed with a 10% citric acid soln. (2×50 ml), the aq. phase reextracted with CHCl$_3$, the combined org. layer dried (MgSO$_4$), evaporated, and co-evaporated with toluene, and the residue precipitated by MeOH and washed with Et$_2$O: 103 mg (86%) of 12. UV (CH$_2$Cl$_2$: 259 (4.16). $^1$H-NMR ((D$_6$)DMSO): 8.33, 8.13 (2s, H—C(8), H—C(2)); 7.68 (t, NH(CH$_2$)$_5$CO); 7.25 (s, NH$_2$); 6.05 (d, H—C(1')); 5.60 (m, H—C(2')); 5.11 (t, OH—C(5')); 4.32 (m, H—C(4')); 3.65, 3.47 (2m, 2 H—C(5')); 2.95 (q, 1 CH$_2$ of NH(CH$_2$)$_5$CO); 2.6, 2.15 (2m, 2 H—C(3')); 2.34, 2.00 (2t, 2 CH$_2$ of NH(CH$_2$)$_5$CO, 2 H of Me(CH$_2$)$_{12}$Co); 1.65–1.15 (m, 28 H, 2 CH$_2$ of NH(CH$_2$)$_5$CO, Me(CH$_2$)$_{12}$CO); 0.83 (t, Me(CH$_2$)$_{12}$CO). Anal. calc. for C$_{30}$H$_{50}$N$_6$O$_5$ ½ H$_2$O (583.76): C 61.72, H 8.81, N. 14.39; found C 62.04, H 9.07, N 13.85.

Preparation 9

3'-Deoxy-2'-O-{6-[(3α, 7α, 12α-trihydroxy-5β-cholan-24-oly)amino]hexanoyl}adenosine (13).

As described in Preparation 8, with 11 (430 mg. 0.454 mmol), 0.5M DBU in abs. pyridine (6.7 ml; 20 h), and AcOH (250 mg, 4.16 mmol). Workup with CHCl$_3$ (200 ml) including a small amount of MeOH, H$_2$O (60 ml), and sat. NaHCO$_3$ soln. (80 ml), reextraction, purification by FC (silica gel, 4×3 cm, CHCl$_3$/MeOH 9:1, then 4:1), and precipitation of the product in petroleum ether gave 269 mg of 13 (78%). UV (MeOH): 259 (4.16). $^1$H-NMR ((D$_6$) DMSO): 8.33, 8.13 (2s, H—C(8), H—C(2)); 7.71 (t, NH(CH$_2$)$_5$CO); 7.31 (s, NH$_2$(ade)); 6.05 (d, H—C(1')); 5.60 (m, H—C(2')); 5.12 (t, OH—C(5')); 4.31 (m, H—C(4'), OH-chol.); 4.07 (d, OH-chol.); 3.98 (d, OH-chol.); 3.77, 3.55, 3.15 (3m, 3 H of chol.); 3.65, 3.47 (m, 2 H—C(5')); 2.98 (m, 1 CH$_2$ of NH(CH$_2$)$_5$CO); 2.6–0.55 (m, 2 H—C(3'), 4 CH$_2$ of NH(CH$_2$)$_5$CO), 33 H of chol.). Anal. calc. for C$_{40}$H$_{62}$N$_6$O$_8$. ½ H$_2$O (763.98): C 62.89, H 8.31, N 11.00; found: C 62.63, 8.28, N 11.26.

Preparation 10a

3'-Deoxy-5'-O-[6-(tetradecanoylamino)hexanoyl] adenosine (16).

As described in Preparation 4, with tetradecanoic acid (151 mg, 0.66 mmol), TOTU (67 mg, 0.66 mmol), and N-methylmorpholine (67, 0.66 mmol) in abs. DMF (3 ml; 1 h). Deblocking of 7 (584 mg, 0.6 mmol) with 3% piperidine in abs. DMF (6 ml; 10 min) and addition of above-mentioned soln. (r.t., 2.5 h). Workup with CHCl$_3$ (150 ml) and NaHCO$_3$ soln. (2×70 ml) and reextraction. Purification by FC (silica gel, 12×3 cm, CHCl$_3$, then CHCl$_3$/MeOH 98:2,95:5): 405 mg (70%) of 14. Colorless oil. $^1$H-NMR (CDCl$_3$): 8.73–8.15 (m, H—C(8), H—C(2), 4 H o to NO$_2$, NH(ade)); 7.47–7.38 (m, 4H m to NO$_2$); 6.12 (d, H—C(1')); 5.73 (m, H—C(2')); 5.57 (t, NH(CH$_2$)$_5$CO); 4.68 (m, H—C (4')); 4.54, 4.43 (2t, 2 OCH$_2$CH$_2$); 4.4–4.2 (m, 2 H—C(5')); 3.7–3.5 (m, 1 CH$_2$ of NH(CH$_2$)$_5$CO); 3.25–3.1 (m, 2 OCH$_2$CH$_2$, 1 CH$_2$ of NH(CH$_2$)$_5$CO); 2.65, 2.25 (2m, 2 H—C(3')); 2.27, 2.15 (2t, 2 CH$_2$ of NH(CH$_2$)$_5$CO), 1 CH$_2$ of Me(CH$_2$)$_{12}$CO); 1.7–1.15 (m, 3 CH$_2$ of NH(CH$_2$)$_5$CO), 11 CH$_2$ of Me(CH$_2$)$_{12}$CO); 0.87 (t, Me(CH$_2$)$_{12}$CO).

Preparation 10b

As described in Preparation 8, with crude 14 (392 mg. 0.408 mmol), 0.5M DBU in abs. pyridine (12ml; 20 h), and AcOH (400 mg, 6.66 mmol). Workup with CH$_2$Cl$_2$ (120 ml) and H$_2$O (2×60 ml), reextraction, co-evaporation of the residue with toluene, and purification by precipitation of the product in petroleum ether gave 202 mg of 16 (86%). Colorless powder. UV (MeOH): 259 (4.16). $^1$H-NMR (CDCl$_3$): 8.22, 8.13 (2s, H—C(8), H—C(2)); 7.68 (br., NH(CH$_2$)$_5$CO); 7.26 (br., NH$_2$(ade)); 5.90 (s, H—C(1')); 5.76 (br., OH—C(2')); 4.69 (m, H—C(2')); 4.53 (m, H—C(4')); 4.3–4.1 (m, 2 H—C(5')); 3.0 (m, 1 CH$_2$ of NH(CH$_2$)$_5$CO); 2.35–2.0 (2m, 2t, 2 H—C(3'), 1 CH$_2$ of NH(CH$_2$)$_5$CO, 1 CH$_2$ of Me(CH$_2$)$_{12}$CO); 1.5–1.1 (m, 3 CH$_2$ of NH(CH$_2$)$_5$CO. 11 CH$_2$ of Me(CH$_2$)$_{12}$CO); 0.83 (t, Me(CH$_2$)$_{12}$CO). Anal. calc. for C$_{30}$H$_{50}$N$_6$O$_5$ (574.76): C 62.69, H 8.77, N 14.62; found: C 62.32, H 8.68, N 14.55.

Preparation 11a

3'Deoxy-5'-O-{6-[(3α, 7α, 12α-trihydroxy-5β-cholan-24-oyl)amino]hexanoyl}adenosine (17).

As described in Preparation 4, with cholic acid (270 mg, 0.66 mmol), TOTU (67 mg, 0.66 mmol). and N-methylmorpholine (67 mg, 0.66 mmol) in abs. DMF (3 ml; 1 h). Deblocking of 7(584 mg, 0.6 mmol) with 3% piperidine in abs. DMF (6 ml; 10 min) and addition of the above-mentioned soln. (r.t., 1.5 h). Workup with CHCl$_3$ (200 ml) and NaHCO$_3$ soln. (2×100 ml), reextraction, and purification by FC (silica gel, 8×3 cm, CHCl3/MeOH 95:5, 93:7 gave 518 mg (ca. 76%) of 15. Amorphous solid. contaminated with cholic acid. $^1$H-NMR (CDCl$_3$): 9.35 (br., NH(ade)); 8.73,8.3–8.15 (s, m, H—C(8), H—C(2), 4 H o to NO$_2$); 7.47–740 (m, 4 H m to NO$_2$); 6.15 (s, H—C(1')); 5.92 (t, NH(CH$_2$)$_5$CO); 5.75 (m, H—C(2')); 4.63 (m, H—C(4')); 4.6–4.2 (m, 2 OCH$_2$CH$_2$, 2 H—C(5')); 4.0–3.25 (m, 6 H of chol.); 3.22–3.1 m, 2 OCH$_2$CH$_2$, 1 CH$_2$ of NH(CH$_2$)5CO); 2.7, 2.5–0.65 (m, 2 H—C(3'), 4 CH$_2$ of NH(CH$_2$)$_5$CO, 33 H of chol.).

Preparation 11b

As described in Preparation 8, with crude 15 (447 mg, 0.392 mmol), 0.5M DBU in abs. pyridine (11.5 ml; 20 h), and AcOH (380 mg, 6.32 mmol). Workup with CHCl$_3$ (200 ml) including a small amount of MeOH, H$_2$O (60 ml), and sat. NaHCO$_3$ soln., reextraction, co-evaporation of the residue with toluene, purification by FC (silica gel, 4×3 cm, CHCl$_3$, then CHCl$_3$/MeOH 9:1, 8:2), and precipitation of the product in petroleum ether: 197 mg of 17 (67%). Colorless powder. UV (MeOH): 259 (4.16). $^1$H-NMR ((D$_6$)DMSO): 8.22, 8.13 (2s, H—C(8), H—C(2)); 7.70 (1, NH(CH$_2$)$_5$CO); 7.28 (s, NH$_2$(ade)); 5.90 (d, H—C(1')); 5.72 (m, OH—C(2')); 4.67 (br., H—C(2'); 4.50 (m, H—C(4')); 4.29, 4.07, 3.99 (3m, 3 OH-chol.); 4.25–4.17 (m, 2 H—C(5')); 3.77, 3.59, 3.17 (3M, 3H of chol.); 3.0 (q, 1 CH$_2$ of NH(CH$_2$)$_5$CO); 2.3–0.55 (m, 2 H—C(3'), 4 CH$_2$ of NH(CH$_2$)$_5$CO), 33 H of chol.). Anal. calc. for C$_{40}$H$_{62}$N$_6$O$_8$·H$_2$O (763.98): C 62.15, H 8.35, N 10.87; found: C 62.36, H 8.27, N 10.65.

Preparation 12

3'-Deoxy-2'-O-{6-{{[(9H-fluoren-9-yl)methoxy]carbonyl}amino}hexanoyl}-N$^6$-[2-(4-nitrophenyl)ethoxycarbonyl]adenosine (18).

To a soln. of 6 (1.052 g, 1 mmol) in abs. CH$_2$Cl$_2$ (20 ml) was added CF$_3$COOH (0.4 ml) and stirred at r.t. for 1 h. Then, MeOH (5 ml) was added, the mixture evaporated and co-evaporated with toluene/MeOH, and the residue purified by FC (silica gel, 14.5×3.5 cm, CH$_2$Cl$_2$, then CH$_2$Cl$_2$/MeOH 98:2, 97:3,95:5, 90:10, 85:15): 535 mg (69%) of 18. Amorphous solid. UV (CH$_2$Cl$_2$): 299 (4.00), 2.86 (sh, 4.10), 272 (sh, 4.55), 2.66 (4.62). $^1$H-NMR (CDCl$_3$): 8.72–8.10 (3s, d, H—C(8), H—C(2), NH, 2 H o to NO$_2$); 7.77–7.27 (m, 8 H of fmoc, 2 H m to NO$_2$); 5.96 (d, H—C(1')); 5.65 (m, H—(2')); 4.90–4.80 (m, NH(CH$_2$)$_5$CO, OH—C(5')) ;4.56–4.22 (m, H—C(4'), OCH$_2$CH$_2$, H—C(9)(fmoc), CH$_2$O(fmoc)); 4.15, 3.72 (2m, 2 H—C(5')); 3.25–3.05 (m, OCH$_2$CH$_2$, 1 CH$_2$ of NH(CH$_2$)$_5$CO); 2.90, 2.30 (2m, 2 H—C(3')); 2.36 (t, 1 CH$_2$ of NH(CH$_2$)$_5$CO); 1.9–1.35 (m, 1 CH$_2$ of NH(CH$_2$)$_5$CO). Anal. calc. for C$_{40}$H$_{41}$N$_7$O$_{10}$ (779.81): C 61.61, H 5.30, N 12.57 found: C 61.65, H 5.37, N 12.53.

Preparation 13

3'-Deoxy-5'-O-(monomethoxytrityl)-N$^6$-[2-(4-nitrophenyl)-ethoxycarbonyl]adenylyl-{2'-{O$^P$-[2-(4-nitrophenyl)ethyl]}→5'}-3'deoxy-2'-O-{6-{{[($^9$H-fluoren-9-yl)methoxy]carbonyl}amino}hexanoyl}-N$^6$-(4-nitrophenyl)ethoxycarbonyl]adenosine (19).

A mixture of 18 (1.46 g, 1.87 mmol), 3'-deoxy-5'-O-(monomethoxytrityl)-N$^6$-[2-(4-nitrophenyl)ethoxycarbonyl]adenosine 2'-[2-(4-nitrophenyl)ethyl diisopropylphosphoramidite][22 (2.28 g, 2.25 mmol) and 1H-tetrazole (656 mg, 9.36 mmol) was stirred in dry MeCN (7 ml) and a few drops of dry CH$_2$Cl$_2$ under N$_2$ at r.t. for 2.5 h. Then it was oxidized with a I$_2$ soln. (I$_2$ (500 mg) in pyridine (3 ml), CH$_2$Cl$_2$ (1 ml), and H$_2$O (1 ml)) until no change of color was detected. The mixture was stirred for 15 min. diluted with CHCl$_3$ (200 ml), and washed with Na$_2$S$_2$O$_3$/NaCl soln. (100 ml) and sat. NaHCO$_3$ soln., the aq. phase reextracted with CHCl$_3$, the combined org. layer dried (MgSO$_4$), evaporated, and co-evaporated with toluene, and the residue purified by FC (silica gel, 16×3 cm, CH$_2$Cl$_2$, CH$_2$Cl$_2$/MeOH 98:2, 97:3, 96:4). Purification had to be repeated for contaminated fractions: 2.858 g (89%) of 19. Amorphous solid. UV (CH$_2$Cl$_2$): 299 (4.26), 286 (sh, 4.47), 272 (sh, 4.83), 266 (4.89), 239 (sh, 4.52). $^1$H-NMR (CDCl$_3$): 8.69–8.10 (m, 2 H—C(8), 2 H—C(2), 2 NH, 6 H o to NO$_2$); 7.76–7.20 (m. 8 H of fmoc, 6 H m to NO$_2$, 12 H of MeOTr); 6.80 (d, 2 H o to MeO); 6.19, 6.02 (d, s, 2 H—C(1')); 5.66, 5.5–5.3 (2m, 2 H—C(2')); 4.95 (m, NH(CH$_2$)$_5$CO); 4.55–4.15 (m, 2 H—C(4'), 3 OCH$_2$CH$_2$, H—C(9)(fmoc), CH$_2$O(fmoc), 2 H—C(5')); 3.77 (s, MeO); 3.5–3.25 (2m, 2 H—C(5')); 3.19–3.00 (m, 3 OCH$_2$CH$_2$, 1 CH$_2$ of NH(CH$_2$)$_5$CO); 2.8–2.15 (m, 4 H—C(3'), 1 CH$_2$ of NH(CH$_2$)$_5$CO); 1.85–1.3 (m, 3 CH$_2$ of NH(CH$_2$)$_5$CO). Anal. calc. for C$_{87}$H$_{83}$N$_{14}$O$_{22}$P (1707.67): C 61.19, H 4.90, N 11.48: found: C 60.99, H 4.98, N 11.20.

Preparation 14

3'-Deoxy-N$^6$-[2-(4-nitrophenyl)ethoxycarbonyl]adenylyl-{2'-{O$^P$-[2-(4-nitrophenyl)ethyl]}→5'}-3'-deoxy-2'-O-{6-{{[(9H-fluoren-9-yl)methoxy]carbonyl}amino}hexanoyl}-N6-[2-(4-nitrophenyl)ethoxycarbonyl]adenosine (20).

As described in Preparation 6, with 19 (2.36 g, 1.38 mmol) and CH$_2$Cl$_2$/MeOH 4:1 (28 ml) containing 2% of TsOH·H$_2$O (45 min). Workup with CHCl$_3$ (150 ml) and sat. NaHCO$_3$ soln. (100 ml), reextraction, and purification by FC (silica gel, 14×3.5 cm, CHCl$_3$, then CHCl$_3$/MeOH 96:4, 95:5, 94:6, 92:8) gave 1.995 g (quant.) of 20. Amorphous solid. UV (CH$_2$Cl$_2$): 299 (4.25), 286 (sh, 4.48), 272 (sh, 4.83), 266 (4.88). $^1$H-NMR ((D$_6$)DMSO): 10.61 (s, 2 NH);

8.62–8.53 (m, 2 H—C(8), 2 H—C(2); 8.15–7.23 (m, 6 H o to NO$_2$, 8 H of fmoc, 6 H m to NO$_2$); 6.19–6.11 (m, 2 H—C(1')); 5.69, 5.15 (2m, 2 H—C(2')); 5.10 (t, OH—C (5')); 4.45–4.05 (m, NH(CH$_2$)$_5$CO, 2 H—C(4'), 3 OCH$_2$CH$_2$, H—C(9)(fmoc), CH$_2$O (fMoc), 2 H—C(5')); 3.65–3.45 (2m, 2 H—C(5')); 3.25–2.85 (m, 3 OCH$_2$CH$_2$, 1 CH$_2$ of NH(CH$_2$)$_5$CO); 2.8–2.0 H—C(3'), 1 CH$_2$ of NH(CH$_2$)$_5$CO); 1.7–1.25 (m, 3 CH$_2$ of NH(CH$_2$)$_5$CO). Anal. calc. for C$_{67}$H$_{66}$N$_{14}$O$_{21}$P (1434.32): C 56.11, H 4.64, N 13.67; found: C 55.99, H 4.75, N 13.34.

Preparation 15

3'-Deoxy-5'-O-(monomethoxytrityl)-N$^6$-[2-(4-nitrophenyl)-ethoxycarbonyl]adenylyl-{2'-{O$^P$-[2-(4-nitrophenyl)ethyl[}→5'}-3'-deoxy-N$^6$-[2-(4-nitrophenyl)ethoxycarbonyl]adenylyl-{2'-{O$^P$-[2-(4-nitrophenyl)ethyl]}→5'}-3'-deoxy-2'-O-{6-{[(9H-fluoren-9-yl)methoxy]carbonyl}amino}hexanoyl}-N$^6$-[2-(4-nitrophenyl)ethoxycarbonyl]adenosine (21)

As described in Preparation 13, with 20 (2.0 g, 1.39 mmol), 3'-deoxy-5'-O-(monomethoxytrityl)-N$^6$-[2-(4-nitrophenyl)ethoxycarbonyl]adenosine 2'-[2-(4-nitrophenyl) ethyl diisopropylphosphoramidite][22](1.766 g, 1.74 mmol), 1 H-tetrazole (478 mg, 6.95 mmol), anh. MeCN (7 ml; 2h), and I$_2$ soln. Workup with CHCl$_3$ (150 ml) and Na$_2$S$_2$O$_3$/NaCl soln. (2×80 ml), reextraction, and purification by FC (silica gel, 7×4.5 cm, CHCl$_3$, then CHCl$_3$/MeOH 97:3, 96:4 gave 3.092 g (94%) of 21. Amorphous solid. UV (CH$_2$Cl$_2$): 297 (4.45), 286 (sh, 4.67), 272 (sh, 5.01), 266 (5.05). $^1$H-NMR ((D$_6$)DMSO): 9.1–8.0 (m, 3 NH, 3 H—C (8), 3 H—C(2), 10 H o to NO$_2$); 7.75–7.15 (m, 8 H of fmoc, 10 H m to NO$_2$, 12 H of MeOTr); 6.78 (d, 2 H o to MeO); 6.19–6.01 (m, 3 H—C(1')); 5.73, 5.45, 5.32 (m, 3 H—C(2')); 5.0 (m, NH(CH$_2$)$_5$CO); 4.6–4.1 (m, 3 H—C(4'), 5 OCH$_2$CH$_2$, H—C(9)(fmoc), CH$_2$O(fmoc), 4 H—C(5')); 3.76 (s, MeO); 3.45, 3.3 (2m, 2 H—C(5')); 3.25–2.95 (m, 5 OCH$_2$CH$_2$, 1 CH$_2$ of NH(CH$_2$)$_5$CO); 2.8–1.9 (m, 6 H—C (3'), 1 CH$_2$ of NH(CH$_2$)$_5$CO); 1.7–1.3 (m, 3 of NH(CH$_2$)$_5$CO). Anal. calc. for C$_{114}$H$_{109}$N$_{21}$O$_{33}$P$_2$ (2363.19): C 57.94, H 4.65, N 12.44; found: C 57.71, H 4.69, N 12.27.

Preparation 16

3'-Deoxy-5'-O-(monomethoxytrityl)-N$^6$-[2-(4-nitrophenyl)ethoxycarbonyl]adenylyl-{2'-{O$^P$-2-(4-nitrophenyl)ethyl]}→5'}-3'-deoxy-N$^6$-[2-(4-nitrophenyl)ethoxycarbonyl]adenylyl-{2'-{O$^P$-2-(4-nitrophenyl)ethyl]}→5'}-3'-deoxy-N$^6$-[2-(4-nitrophenyl)ethoxycarbonyl]-2'-O-[6-(tetradecanoylamino)hexanoyl]adenosine (22).

As described in Preparation 4, with tetradecanoic acid (38 mg, 0.165 mmol), TOTU (54 mg, 0.165 mmol), and N-methylmorpholine (17 mg, 0.165 mmol) in abs. DMF (1.5 ml; 1 h). Deblocking of 21 (354 mg, 0.15 mmol) with 3% piperidine in abs. DMF (2 ml; 10 min) and addition of the above-mentioned soln. (r.t., 3 h), more preactivated tetradecanoic acid (38 mg, 0.165 mmol), TOTU (54 mg, 0.165 mmol), and N-methylmorpholine (17 mg, 0.165 mmol) in abs. DMF (1.5 ml; 1.5 h). Workup with AcOEt (100 ml) and NaHCO$_3$ soln. (2×50 ml), reextraction, and purification by FC (2×, silica gel, 12×3 cm, CHCl$_3$, then CHCl$_3$/MeOH 98:2, 97:3, 96:4, 95:5) gave 257 mg (73%) of 22. Amorphous solid. UV (CH$_2$Cl$_2$): 272 (sh, 4.92), 267 (4.95), 239 (sh, 4.60). $^1$H-NMR (CDCl$_3$): 8.65–8.0 (m, 3 H—C(8), 3 H—C(2), 10 H o to NO$_2$); 7.5–7.15 (m, 10 H m to NO$_2$, 12 H of MeOTr); 6.78 (d, 2 H o to MeO); 6.21–5.98 (m, 3 H—C(1')); 5.75–5.25 (m, 3 H—C(2')); 4.65–4.1 (m, 3 H—C(4'), 5 OCH$_2$CH$_2$, 4 H—C(5'), NH(CH$_2$)$_5$CO); 3.78 (s, MeO); 3.7–0.85 (m, 2 H—C(5'), 5 OCH$_2$CH$_2$, NH(CH$_2$) $_5$CO, 6 H—C(3'), Me(CH$_2$)$_{12}$CO). Anal. calc. for C$_{113}$H$_{125}$N$_{21}$O$_{32}$P$_2$ (2351.31): C 57.72, H 5.36, N 12.51; found: C 57.58, H 5.43, N 12.51.

Preparation 17

3'-Deoxy-5'-O-(monomethoxytrityl)-N$^6$-[2-(4-nitrophenyl)-ethoxycarbonyl]adenylyl-{2'-{O$^P$-[2-(4-nitrophenyl)ethyl]}→5'}-3'-deoxy-N$^6$-[2-(4-nitrophenyl)ethoxycarbonyl]adenylyl-{2'-(O$^P$-[2-(4-nitrophenyl)ethyl]}→5'}-3'-deoxy-N$^6$-[2-(4-nitrophenyl)ethoxycarbonyl]-2'-O-{6-[(3α,7α,12α-trihydroxy-5-βcholan-24-oyl)amino]hexanoyl}adenosine (23).

As described in Preparation 4, with cholic acid (67 mg, 0.165 mmol), TOTU (54 mg, 0.165 mmol) and N-methylmorpholine (17 mg, 0.165 mmol) in abs. DMF (1.5 ml; 1 h). Deblocking of 21 (354 mg, 0.15 mmol) with 3% piperidine in abs. DMF (2 ml; 10 min) and addition of the above-mentioned soln. (r.t., 3h), more pre-activated cholic acid (34 mg, 82.5 μmol), TOTU (27 mg, 82.5 μmol), and N-methylmorpholine (9 mg, 82.5 μmol) in abs. DMF (1 ml; 1.5 h). Workup with CHCl$_3$ (100 ml) and NaHCO$_3$ soln. (50 ml), reextraction and purification by FC (several times, silica gel, CHCl$_3$, then CHCl$_3$/MeOH 98:2, 93:7, 90:10, 85:15) gave 260 mg (69%) of 23. Amorphous solid. UV (CH$_2$Cl$_2$): 272 (sh, 4.90), 267 (4.94) 240 (sh. 4.58). Anal. calc. for C$_{123}$H$_{137}$N$_{21}$O$_{35}$P$_2$ (2531.51): C 58.36, H 5.45, N 11.62; found: C 58.35, H 5.7, N 10.91.

EXAMPLE 1

3'-Deoxyadenylyl-(2'-5')-3'-deoxyadenylyl-(2'-5')-3'-deoxy-2'-O-[6-(tetradecanoylamino)-hexanoyl] adenosine (24).

A mixture of 22 (80 mg, 34 μmol) in CH$_2$Cl$_2$/MeOH 4:1 (4 ml) containing 2% TsOH . H$_2$O was stirred at r.t. for 20 min. Then the mixture was diluted with CHCl$_3$ (30 ml) and washed with sat. NaHCO$_3$ soln. (2×10 ml), the aq. phase reextracted with CHCl$_3$, and the combined org. layer dried (MgSO$_4$) and evaporated. The crude product was diluted with a small amount of CHCl$_3$ and precipitated from Et$_2$O (15 ml), centrifugated, and dried. For further deblocking, the precipitate was co-evaporated twice with abs. pyridine, then 0.5 M DBU in abs. pyridine was added and the mixture stirred at r.t. for 2 d. Then AcOH (60 mg, 1 mmol) was added, the mixture evaporated and co-evaporated with abs. dioxane, and the product precipitated from dioxane/Et$_2$O 1:3, washed, and centrifugated several times with dioxane/Et$_2$O: 35 mg of 24 (882 OC). Colorless powder. HPLC (0–100% MeCN (0–20 min) in 0.1M (Et$_3$NH)OAc buffer (pH 7)); $t_R$ 14.94 min.

EXAMPLE 2

3'-Deoxyadenylyl-(2',5')-3'-deoxyadenylyl-(2'-5')-3'-deoxy-2'-O-{[(3α,7α,12α-trihydroxy-5β-cholan-24-oyl)-amino]hexanoyl}adenosine (25).

As described in Example 2 with 23 (90 mg, 36 μmol) and CH$_2$Cl/MeOH 4:1 containing 2% TsOH H$_2$O (4 ml; 20 min). Workup with CHCl$_3$ (30 ml) and sat. NaHCO$_3$ soln. (2×10 ml), reextraction, and precipitation from Et$_2$O (15 ml) gave a colorless powder. Treatment with 0.5M DBU in abs. pyridine (1 ml; 2d) and AcOH (60 mg, 1 mmol), workup with abs. dioxane, and precipitation with abs. MeCN/Et$_2$O gave 45 mg of 25 (965 OD). Colorless powder. HPLC (0–100% MeCN (0–20 min) in 0.1M (Et$_3$NH)OAc buffer (pH 7)); $t_R$ 11.81 min.

EXAMPLE 3

3'-Deoxyadenylyl-(2'-5')-3'-deoxyadenylyl-(2'-5')-2'-O-{6-{{N-{4-{[(2-amino-3, 4-dihydro-4-oxopteridin-6-yl)methyl]amino}benzoyl}-L-γ-glutamyl}amino}hexanoyl}-3'deoxy]adenosine (26).

For acid-activation, a mixture of folic acid (3×44 mg, 0.1 mmol), EDC (3×23 mg, 0.12 mmol), and DMAP (3×15 mg, 0.12 mmol) in abs. DMF (3×2.5 ml) was kept at r.t. for 3 h. Trimer 21 (115 mg, 0.05 mmol) was treated with a soln. of 3% piperidine in abs. DMF (2 ml; 15 min) and then evaporated. The above-mentioned soln. was added in 3 portions within 3 h and further stirred for 1 h at r.t., then the mixture was evaporated. The residue was treated with Et$_2$O/CH$_2$Cl$_2$ and the yellow residue washed and centrifugated with CH$_2$Cl$_2$ and Et$_2$O. Then the residue was co-evaporated with abs. pyridine and dissolved in abs. pyridine (5 ml). DBU (380 mg, 2.5 mmol) was added and the mixture stirred at r.t. for 18 h. Then AcOH (300 mg, 5 mmol) was added, the mixture evaporated and the residue treated with 80% AcOH/H$_2$O (10 ml, 17 h). The mixture was centrifugated, the supernatant evaporated, and the residue treated with MeCN. The obtained yellow crude product (27 mg) was purified by prep. HPLC (Lichrospher 100 RP 18, 10 μm, 25×2 cm, 10% MeCN (0–5 min), 10–35% MeCN (5–40), 35–50% (40–45 min), 50% MeCN (45–50 min) in 0.1 M (Et$_3$NH)OAc buffer (pH 7), 7 ml/min): 9 mg (228 OD) of 26. Yellow powder. HPLC (0–50% MeCN (2–32 min) in 0.1 M (Et$_3$NH)OAc buffer (pH 7)): $t_R$ 16.00 min. FAB-MS (matrix glycerol/3-nitrobenzyl alcohol 1:1): (MH$^+$; calc. 1414.5).

Preparation 18

3'-Deoxy-5'-O-{6-{{[(9H-fluorenyl-9-methoxy] carbonyl}amino}hexanoyl}-N$^6$-[2-(4-nitrophenyl) ethoxycarbonyl]adenylyl-2'-{O$^P$-[2-(4-nitrophenyl) ethyl]}→5'}-3'-deoxy-N$^6$-[2-(4-nitropheny l) ethoxycarbonyl]-adenylyl-{2'-{O$^P$-[2-(4-nitrophenyl)ethyl]}→5'}-3'-deoxy-N$^6$,2-O-bis [2-(4-nitrophenyl)ethoxycarbonylladenosine (28).

As described in Preparation 2, with 3'-deoxy-N$^6$-[2-(4-nitrophenyl)ethoxycarbonyl]adenylyl-{2'}O$^P$-[2-(4-nitrophenyl)ethyl]}→5'}3'-deoxy-N$^6$-[2-(4-nitrophenyl) ethoxycarbonyl]adenylyl-{2'-{O$^P$-[2-(4-nitrophenyl)ethyl] }5'}-3'-deoxy-N$^6$, 2'-O-bis[2-(4-nitrophenyl) ethoxycarbonyl]adenosine (27; 2.533 g, 1.3 mmol) [20], 3 (505 mg, 1.43 mmol), EDC (274 mg, 1.43 mmol), DMAP (175 mg, 1.43 mmol), and CH$_2$Cl$_2$ (18 ml; 2.5 h), then more 3 (124 mg, 0.35 mmol), ECD (67 mg, 0.35 mmol), and DMAP (43 mg, 0.35 mmol; 3 h). Workup with CH$_2$Cl$_2$ (200 ml) and 10% citric acid soln. (100 ml), reextraction, sat. NaHCO$_3$ soln. (100 ml), reextraction and purification by FC (silica gel, CHCl$_3$+3% MeOH gave 2.347 g (79%) of 28. Amorphous solid. UV (CH$_2$Cl$_2$): 298 (sh, 4.46), 285 (sh, 4.71), 272 (sh, 5.01), 267 (5.06). $^1$H-NMR (CDCl$_3$): 8:65–8.0 (m, 3 H—C(8), 3 H—C(2), 12 H o to NO$_2$); 7.75–7.2 (m, 8 H of fmoc, 12 H m to NO$_2$); 6.15–5.98 (m, 3 H—(1')); 5.7–5.15 (m, 3 H—C(2')); 4.65–4.05 (m, NH(CH$_2$)$_5$CO, 3 H—C(4'), 6 OCH$_2$CH$_2$, H—C(9)(fmoc), CH$_2$O(fmoc), 6 H—C(5')); 3.2–2.9 (m, 6 OCH$_2$CH$_2$, 1 CH$_2$ of NH(CH$_2$)$_5$CO); 2.7 (m, H—C(3')); 2.4–2.1 (m, 5 H—C (3'), 1 CH$_2$ of NH(CH$_2$)$_5$CO); 1.65–1.25 (m, 3 CH$_2$ of NH(CH$_2$)$_5$CO). Anal. calc. for C$_{103}$H$_{100}$N$_{22}$O$_{36}$P$_2$ (2284.00): C 54.17, H 4.41, N 13.49; found: C 54.25, H 4.53, N 13.03.

Preparation 19

3'-Deoxy-N$^6$-[2-(4-nitrophenyl)ethoxycarbonyl]-5'-O-[6-(tetradecanoylamino)hexanoyl]adenylyl-2'-{O$^P$-[2-(4-nitrophenyl)ethyl)}→5'}3'-deoxy-N$^6$-[2-(4-nitrophenyl)ethoxycarbonyl]adenylyl-{2'-{O$^P$-[2-(4-nitrophenyl)ethyl]→5'}-3'-deoxy-N$^6$, 2'-O-bis[2-(4-nitrophenyl)ethoxycarbonyl]adenosine (29).

As described in Preparation 4, with tetradecanoic acid (40 mg, 0.176 mmol), TOTU (56 mg, 0.176 mmol), and N-methylmorpholine (18 mg, 0.176 mmol) in abs. DMF (1.5 ml; 1 h). Deblocking of 28 (265 mg, 0.16 mmol) with 3% piperidine in abs. DMF (4 ml; 15 min) and addition of the above-mentioned soln. (r.t., 1.5 h), more pre-activated tetradecanoic acid (40 mg, 0. 176 mmol), TOTU (58 mg, 0.176 mmol), and N-methylmorpholine (18 mg, 0.176 mmol) in abs. DMF (1.5 ml; 1.5 h). Workup with CHCl$_3$ (100 ml) and NaHCO$_2$ soln. (50 ml), reextraction, and purification by FC (2×, silica gel, 13.5×2 cm, CHCl$_3$, then CHCl$_3$/MeOH 96:4, 94:6) gave 272 mg (75%) of 29. Amorphous solid. UV (CH$_2$Cl$_2$): 272 (sh, 4.96), 267 (4.99). $^1$H-NMR (CDCl$_3$): 9.15–8.05 (m, 3 NH(ade), 3 H—C(8), 3 H—C(2), 12 H o to NO$_2$); 7.5–7.2 (m, 12 H m to NO$_2$); 6.15–5.95 (m, 3 H—C(1')); 5.7–5.25 (m, 3 H(2')); 4.65–4.1 (m, 3 H—C(4'), 6 OCH$_2$CH$_2$, 6 H—C(5'), NH(CH$_2$)$_5$CO); 3.3–3.0 (m, 6 OCH$_2$CH$_2$, 4 CH$_2$ of NH(CH$_2$)$_5$CO); 3.0–2.0 (m, 6 H—C (3'), 1 CH$_2$ of Me(CH$_2$)$_{12}$CO); 1.7–1.2 (m, 3 CH$_2$ of NH(CH$_2$)$_5$CO, 10 CH$_2$ of Me(CH$_2$)$_{12}$CO); 0.87 (t, Me(CH$_2$)$_{12}$CO). Anal. calc. for C$_{102}$H$_{116}$N$_{22}$O$_{35}$P$_2$ (2272.12): C 53.92, H 5.15, N 13.56; found: C 53.72, H 5.19, N 13.41.

Preparation 20

3'-Dexoy-N$^6$-[2(4-nitrophenyl)ethoxycarbonyl]-5'-O-{6-[(3α,7α, 12α-trihydrox-5β-cholan-24-oyl) amino]-hexanoyl}adenylyl-{2'-{O$^P$[2-(4-nitrophenyl)ethyl]}→5'}-3'-deoxy-N$^6$-[2-(4-nitrophenyl)ethoxycarbonyl]adenylyl-{2'-O$^P$-[2-(4-nitrophenyl)ethyl]}→5'}-3'-deoxy-N$^6$, 2'-O-bis[2-(4-nitrophenyl)ethoxycarbonyl]adenosine (30).

As described in Preparation 4, with cholic acid (54 mg, 0.132 mmol), TOTU (43 mg, 0.132 mmol), and N-methylmorpholine (14 mg, 0.132 mmol) in abs. DMF (1.5 ml; 1 h). Deblocking of 28 (275 mg. 0.12 (mmol) with 3% piperidine in abs. DMF (2 ml; 20 min) and addition of the above-mentioned soln. (r.t., 1.5 h), more preactivated cholic acid (54 mg, 0.132 mmol), TOTU (43 mg; 0.132 mmol), and N-methylmorpholine (14 mg, 0.132 mmol) in abs. DMF (1 ml; 1.5 h). Workup with CHCl$_3$ (100 ml) and NaHCO$_3$ soln. (50 ml), reextraction, and purification by FC (several times, silica gel, CHCl$_3$, then CHCl$_3$/MeOH 95:5, 90:5, 85:15) gave 195 mg (69%) of 30. Amorphous solid. UV (CH$_2$Cl$_2$): 272 (sh, 4.96), 268 (4.99). Anal. calc. for C$_{112}$H$_{128}$N$_{22}$O$_{38}$P$_2$ (2452.32): C 54.68, H 5.26, N 12.57; found: C 55.17, H 5.51, N 11.86.

EXAMPLE 4

3'-Deoxy-5'-O-[6-(tetradecanoylamino)hexanoyl] adenylyl-(2'-5')-3'-deoxyadenylyl-(2'-5')-3'-deoxyadenosine (31).

Trimer 29 (85 mg, 37 μmol) was first co-evaporated with abs. pyridine. Then 0.5 M DBU in abs. pyridine (1.3 ml) was added and the mixture stirred at r.t. for 2 d. Then AcOH (80 mg, 1.3 mmol) was added, the mixture evaporated and co-evaporated with abs. dioxane, and the product precipitated from dioxane/$Et_2O$ 1:3, washed, and centrifugated with dioxane/$Et_2O$: 45 mg of 31 (1166 OD). Colorless powder. HPLC (0–100% MeCN (0–20 min) in 0.1 M ($Et_3NH$)OAc buffer (pH 7)): $t_R$ 14.98 min.

EXAMPLE 5

3'-Deoxy-5'-O-{6-[(3α, 7α, 12α-trihydroxy-5β-cholan-24-oyl)amino]hexanoyl}adenylyl-(2'-5')-3'-deoxyadenylyl-(2'-5')-3'-deoxyadenosine (32).

As described in Example 4, with 30 (50 mg, 20, mol), 0.5 M DBU in abs. pyridine (0.8 ml; r.t.; 2 d), and AcOH (60 mg, 1 mmol). Workup with abs. dioxane, precipitation with abs. MeCN, and washing with abs. MeCN and $Et_2O$: 32 mg of 32 (639 OD). Colorless powder. HPLC (0–100% MeCN (0–20 min) in 0.1 M ($Et_3NH$)OAc buffer (pH 7)); $t_R$ 11.75 min.

EXAMPLE 6

5'-O-{6-{{N-{4-{[(2-Amino-[3, 4-dihydro-4-oxopteridin-6-yl)methyl]amino}benzoyl}-L-γ-glutanyl}amino}hexanoyl}-adenylyl-(2'-5')-3'-deoxyadenylyl-(2'-5')-3'-deoxyadenosine (33).

As described in Example 3, with folic acid (3×44 mg, 0.1 mmol). ECD (3×23 mg, 0.12 mmol), and DMAP (3×15 mg, 0.12 mmol) in abs. DMF (3×2.5 ml; r.t., 3 h). Deblocking of trimer 28 (111 mg, 0.05 mmol) with 3% piperidine in abs. DMF (2 ml; 15 min) and addition of the above-mentioned soln. (3 portions within 4 h). Workup with $Et_2O$/$CH_2Cl_2$, then washing and centrifugation with $CH_2Cl_2$ and $Et_2O$, further deblocking by DBU treatment (380 mg, 2.5 mmol) in abs. pyridine (5 ml; 18 h), addition of AcOH (300 mg, 5 mmol), evaporation, and treatment with 80% AcOH/$H_2O$ (10 ml, 17 h). The mixture was centrifugated and the supernatant evaporated and treated with MeCN: yellow powder (19 mg). Purification by prep. HPLC (Lichrospher 100 RP18, 10 µm, 25×2 cm, 10% MeCN (0–5 min), 10–35% MeCN (5–40 min), 35–50% MeCN (40–45 min), 50% MeCN (45–50 min) in 0.1 M ($Et_3NH$)OAc buffer (pH 7), 7 ml/min): 43 OD of 33. Yellow amorphous solid. HPLC (0–50% MeCN (0–20 min), 50–75% MeCN (20–25 min) in 0.1 M ($Et_3NH$)OAc buffer (pH 7)): $t_R$ 11.86 min. FAB-MS (matrix glycerol/3-nitrobenzyl alcohol 1:1): 1414 ($MH^+$; calc. 1414.5).

Phosphorylation of Core Compounds

The core compounds of the present invention may be 5'-monophosphorylated according to the procedure of Sambrook et al., *Molecular Cloning—A Laboratory Manual*, 2 ed., Cold Spring Harbor Laboratory Press, pp. 5.68–5.71 (1989) with ATP with T4 polynucleotide kinase. 5'-Monophosphorylation may be determined by reverse-phase HPLC analysis and confirmed by the subsequent hydrolysis of each 5'-monophosphate derivative by 5'-nucleotidase. Yields of phosphorylation range from 15% to 60%. In the case where the $R_2$ groups of all internucleotide bonds (Formula I) of the molecule comprise oxygen, i.e., the linkages comprise phosphodiester bonds, the 5'-monophosphates are readily prepared by reacting the corresponding unphosphorylated core compound with $POCl_3$.

The 5'-diphosphate and 5'-triphosphate of the core compounds of the invention may be prepared by following the procedure of Example 7.

EXAMPLE 7

All reactions are performed in glassware oven-dried at 125° C. for 18–24 hr. Core compound (400 OD units at 260 run) is dissolved in 500 microliters of dry dimethylformamide ("DMF") and dried in vacuo in a 10 ml conical flask at 35° C. This process is repeated three times. To the dry residue, 50 micromoles of triphenylphosphine, 100 micromoles of imidazole and 50 micromoles of dipyridinyl disulfide are added. The mixture is dissolved in 500 microliters dry DMF plus 50 microliters of dry dimethylsulfoxide. The solution is stirred with a stirring bar for 2 hr at room temperature. After 2 hr the solution is homogeneous (after 30 minutes, the solution begins to change to yellow). The solution is transferred dropwise to 10 ml of a 1% NaI/dry acetone (w/v) solution. The clear colorless precipitate which forms is the sodium salt of the 5'-phosphoroimidazolidate. The precipitate is centrifuged at room temperature, the supernatant is decanted, and the precipitate is washed three times with 10 ml dry acetone. The centrifuging is repeated. The precipitate is dried over $P_2O_5$ in vacuo for 2 hr. The precipitate is dissolved in 200 microliters of freshly prepared 0.5 M tributylammonium pyrophosphate in dry DMF. The solution is maintained at room temperature for 18 hr after which time the DMF is removed in vacuo. The residue is dissolved in 0.25 M triethylammonium bicarbonate buffer ("TEAB") (pH 7.5). The 5'-di and 5'-triphosphate products are separated using a DEAE-Sephadex A25 column ($HCO_3^-$-form; 1×20 cm) with a linear gradient of 0.25 M to 0.75 M TEAB. Fractions (10 ml) are collected. The product is observed by ultraviolet spectroscopy at 254 nm. The fractions containing the 5'-di and 5'-triphosphates are separately pooled and dried in vacuo. The TEAB is removed by repeated addition of water followed by lyophilization. The yield of the 5'-diphosphate is about 5%; the yield of the 5'-triphosphate is about 60%.

All references cited with respect to synthetic, preparative and analytical procedures are incorporated by reference.

The present invention may be embodied in other specific forms without departing from the spirit or essential attributes thereof and, accordingly, reference should be made to the appended claims, rather than to the foregoing specification, as indication the scope of the invention.

References

[1] C. Hörndler, R. J. Suhadolnik, N. F. Muto, E. E. Henderson, M. X. Guan, W. Pfleiderer, *Helv. Chim. Acta* 1997, 80, in press.

[2] B. R. G. Williams, R. R. Golger, R. E. Brown, C. S. Gilbert, I. M. Kerr, *Nature* 1979, 282, 582.

[3] P. Lengyel, *Annu. Rev. Biochem.* 1982, 51, 251.

[4] A. G. Hovanessian, *J. Interferon Res.* 1991, 11, 199.

[5] H. C. Schröder, R. J. Suhadolnik, W. Pfleiderer, R. Charubala, W. E. G. Müller, *Int. J. Biochem.* 1992, 24, 55.

[6] B. A. Hassell, A. Zhon, R. H. Silverman, *Cell* 1993, 72, 753.

[7] R. Charubala, W. Pfleiderer, *Tetrahedron Lett.* 1980, 21, 4077.

[8] R. Charubala et al., *Helv. Chim. Acta* 70:2028 (1987)

[9] P. W. Doetsch et al., *Proc. Natl. Acad. Sci. USA* 78:6699 (1981)

[10] H. Sawai et al., *J. Biol. Chem.* 258:1671 (1983)

[11] W. E. G. Müller et al., *Biochemistry* 30:2027 (1991)

[12] C. Barat et al., *EMBO J* 8:3279 (1989)

[13] Progress in Molecular and Subcellular Biology, Biological Response Modifiers—Interferons, Doublestranded RNA and 2'-5'-Oligoadenylates, Eds. W. E. G. Müller et al., Springer Verlag, Berlin, 1994, Vol. 14.

[14] K. Renneisen et al., *J. Biol. Chem.* 265:16337 (1990)
[15] J. Goodchild et al., *Bioconjugate Chem.* 1:165 (1990) and ref. cit. therein.
[16] S. L. Beaucage et al., *Tetrahedron* 49:1925 (1993)
[17] M. Manoharan et al., *Tetrahedron Lett* 32:7171 (1991)
[18] M. Wasner et al., *Helv. Chim. Acta* 77:1757 (1994)
[19] M. Wasner et al., *Helv. Chim. Acta* 79:609 (1996)
[20] M. Wasner et al., *Helv. Chim. Acta* 79:619 (1996)
[21] D. G. Norman et al., *Synthesis* 304 (1983)
[22] H. Schirmeister et al., *Helv. Chim. Acta* 77:10 (1994)
[23] C. P. Leamon et al., *Proc. Natl. Acad. Sci. USA* 88:5572 (1991)

What is claimed is:

1. A compound according to the formula

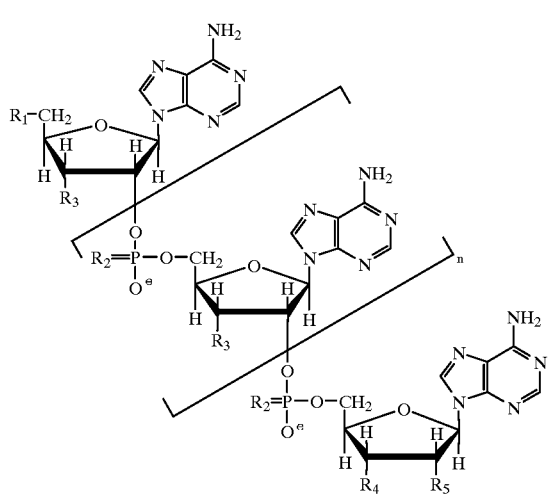

(I)

wherein:

n is from 1 to 8;

$R_1$ is selected from the group consisting of

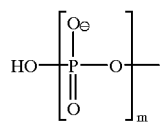

wherein m is zero, 1, 2, or 3; and

wherein q is from 1 to 20;

$R_2$ is independently selected from the group consisting of oxygen and sulfur;

$R_3$ is independently selected from the group consisting of hydrogen and hydroxyl; and $R_4$ is selected from the group consisting of hydrogen, hydroxyl and

$R_5$ is selected from the group consisting of hydroxyl and

$R_6$ is selected from the group consisting of

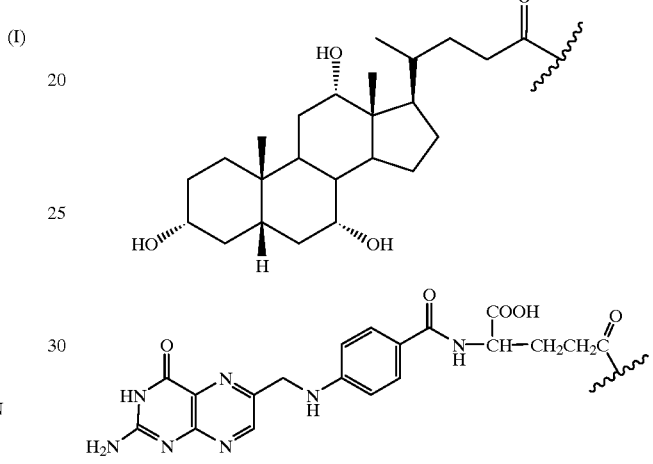

and

wherein x is from 1 to 20; provided that one of $R_1$, $R_4$ and $R_5$ is

wherein $R_6$ is defined as above; or water soluble salt thereof.

2. A compound according to claim 1 wherein $R_1$ is

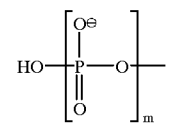

and m is 3.

3. A compound according to claim 1 wherein $R_1$ is $$HO-\left[\begin{array}{c}O^{\ominus}\\|\\P-O\\||\\O\end{array}\right]_m$$

and m is 1.

4. A compound according to claim 1 wherein $R_1$ is $$HO-\left[\begin{array}{c}O^{\ominus}\\|\\P-O\\||\\O\end{array}\right]_m$$

and m is 0.

5. A compound according to any preceding claim wherein n is 1 or 2.

6. A compound according to claim 5 wherein each $R_3$ is hydrogen and each $R_2$ is oxygen.

7. A compound according to claim 6 wherein q is from 2 to 8.

8. A compound according to claim 6 wherein q is from 3 to 7.

9. A compound according to claim 6 wherein q is from 2 to 8 and x, if present, is from 2–16.

10. A compound according to claim 9 wherein $R_6$ is myristoyl.

11. A compound according to claim 9 wherein $R_6$ is

[structure: pteridine-benzoyl-glutamyl group]

12. A compound according to claim 9 wherein $R_6$ is

[structure: cholanoyl / bile acid group]

13. A compound according to claim 10 selected from the group consisting of 3'-deoxyadenylyl-(2'-5')-3'-deoxyadenylyl-(2'-5')-3'-deoxy-2'-O-[6-(tetradecanoylamino)-hexanoyl]adenosine, the 5'-mono-, di-, and triphosphates thereof, and water-soluble salts of any of them.

14. A compound according to claim 10 selected from the group consisting of 3'-deoxy-5'-O-[6-(tetradecanoylamino)hexanoyl]adenylyl-(2'-5')-3'-deoxyadenylyl-(2'-5')-3'-deoxyadenosine and water-soluble salts thereof.

15. A compound according to claim 11 selected from the group consisting of 3'-deoxyadenylyl-(2'-5')-3'-deoxyadenylyl-(2'-5')-2'-O-{6-{{N-{4-{[(2-amino-1,4-dihydro-4-oxopteridin-6-yl)methyl[amino}benzoyl}-L-γ-glutanyl}amino}hexanoyl}-3'deoxy]adenosine, the 5'-mono-, di-, and triphosphates thereof, and water-soluble salts of any of them.

16. A compound according to claim 11 selected from the group consisting of 5'-O-{6-{{N-{4-{[(2-amino-3,4-dihydro-4-oxopteridin-6-yl)methyl]amino}benzoyl}-L-γ-glutanyl}amino}hexanoyl}-adenylyl-(2'-5')-3'-deoxyadenylyl-(2'-5')-3'-deoxyadenosine, and water-soluble salts thereof.

17. A compound according to claim 12 selected from the group consisting of 3'-deoxyadenylyl-(2',5')-3'-deoxyadenylyl-(2'-5')-3'-deoxy-2'-O-{-[(3α, 7α, 12α-trihydroxy-5β-cholan-24-oyl)-amino]hexanoyl}adenosine, the 5'-mono-, di-, and triphosphates thereof, and water-soluble salts of any of them.

18. A compound according to claim 12 selected from the group consisting of 3'-deoxy-5'-O-{6-[(3α, 7α, 12α-trihydroxy-5β-cholan-24-oyl)amino]hexanoyl}adenylyl-(2'-5')-3'-deoxyadenylyl-(2'-5')-3'-deoxyadenosine, and water-soluble salts thereof.

19. A compound or water-soluble salt according to any of claims 13, 14, 15, 16, 17 or 18 wherein m is zero.

20. An antiviral composition comprising a compound or water-soluble salt thereof according to claim 1 in combination with an agricultural carrier.

21. An antiviral composition comprising a compound or water-soluble salt thereof according to claim 1 in combination with a pharmaceutical carrier.

22. A method of treating viral infection in a plant comprising administering thereto an antiviral effective amount of a compound or water-soluble salt thereof according to claim 1.

23. A method of treating viral infection in a mammal comprising administering thereto an antiviral effective amount of a compound or water-soluble salt thereof according to claim 1.

* * * * *